United States Patent
Kokuryo et al.

(10) Patent No.: US 8,089,365 B2
(45) Date of Patent: Jan. 3, 2012

(54) WIPER CONTROL METHOD AND WIPER CONTROL DEVICE

(75) Inventors: Kazuto Kokuryo, Ohtsu (JP); Yoshiteru Makino, Ohtsu (JP); Satoshi Furusawa, Minato-ku (JP)

(73) Assignee: Niles Co., Ltd., Tokyo (JP)

( * ) Notice: Subject to any disclaimer, the term of this patent is extended or adjusted under 35 U.S.C. 154(b) by 1302 days.

(21) Appl. No.: 10/556,699

(22) PCT Filed: May 13, 2004

(86) PCT No.: PCT/JP2004/006815
§ 371 (c)(1),
(2), (4) Date: Apr. 10, 2007

(87) PCT Pub. No.: WO2004/101334
PCT Pub. Date: Nov. 25, 2004

(65) Prior Publication Data
US 2008/0211679 A1 Sep. 4, 2008

(30) Foreign Application Priority Data
May 15, 2003 (JP) ................................. 2003-136897

(51) Int. Cl.
*G08B 21/00* (2006.01)
(52) U.S. Cl. ........................ 340/604; 340/2.5; 340/648
(58) Field of Classification Search ............... 340/2.5, 340/604, 648, 605, 618, 641, 691.6, 632, 340/815.45
See application file for complete search history.

(56) References Cited

U.S. PATENT DOCUMENTS

| | | | | |
|---|---|---|---|---|
| 5,216,341 A | * | 6/1993 | Nomura et al. | 318/444 |
| 6,239,570 B1 | * | 5/2001 | Tanaka et al. | 318/483 |
| 2003/0030393 A1 | * | 2/2003 | Morishita et al. | 318/254 |

FOREIGN PATENT DOCUMENTS

| | | |
|---|---|---|
| EP | 1 113 260 | 7/2001 |
| JP | 60 047744 | 3/1985 |
| JP | 60-047744 A | 3/1985 |
| JP | 05-229403 A | 9/1993 |
| JP | 06-328998 A | 11/1994 |
| JP | 2003 002171 | 1/2003 |
| JP | 2003-002171 A | 1/2003 |
| WO | WO 02/55351 | 7/2002 |

OTHER PUBLICATIONS

International Search Report dated Aug. 17, 2009.
Microfilm of the specification and dwgs. Annexed to the request of Japanese Utility Model App. No. 088555/1983 (laid-open No. 192451/1984), Nissan Motor Co., Ltd., Dec. 20, 1984, Full Text.

* cited by examiner

*Primary Examiner* — Daniel Previl
(74) *Attorney, Agent, or Firm* — RatnerPrestia

(57) ABSTRACT

A wiper control method and a wiper control device which can stabilize wiping rhythm of a wiper while ensuring required wiping and smoothly respond to change of a rainfall situation are provided. An adhesion cycle of a raindrop adhering on a detection surface is detected, a current adhesion cycle to be the basis when determining an intermittence time of a wiper is determined based on the detected raindrop adhesion cycle, the wiper intermittence time is determined based on the current adhesion cycle, a raindrop adhesion cycle shorter than the current adhesion cycle is detected, and when the raindrop adhesion cycle shorter than the current adhesion cycle is detected a predetermined number of times, the current adhesion cycle is changed to a shorter adhesion cycle and the wiper intermittence time is determined based on the changed current adhesion cycle.

10 Claims, 32 Drawing Sheets

| RAINFALL STATE | MODE / STEP | SHORT | MEDIUM | LONG |
|---|---|---|---|---|
| HEAVY RAIN | 1 | Hi | Hi | Hi |
| | 2 | Lo | Lo | Lo |
| | 3 | 1 | 1.5 | 3 |
| | 4 | 2 | 3 | 6 |
| | 5 | 4 | 6 | 12 |
| | 6 | 8 | 12 | 24 |
| DRIZZLING RAIN | 7 | 16 | 24 | 48 |

INTERMITTENCE TIME WOT (SECONDS)

FIG. 11

|  | FIRST | SECOND | THIRD |
|---|---|---|---|
| EDGE | 1 | 1 |  |
| ZONE | B | C |  |

|  | FIRST | SECOND | THIRD |
|---|---|---|---|
| EDGE | 1 | 1 | 1 |
| ZONE | B | C | B |

|  | B | C | D | E |
|---|---|---|---|---|
| CURRENT ZONE | 0 | 1 | 0 | 0 |

FIG. 22
(A)
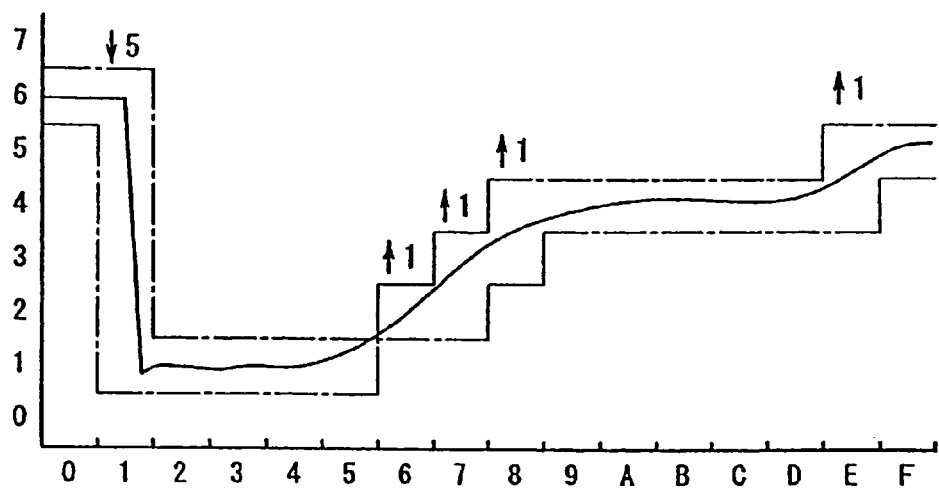
(B)
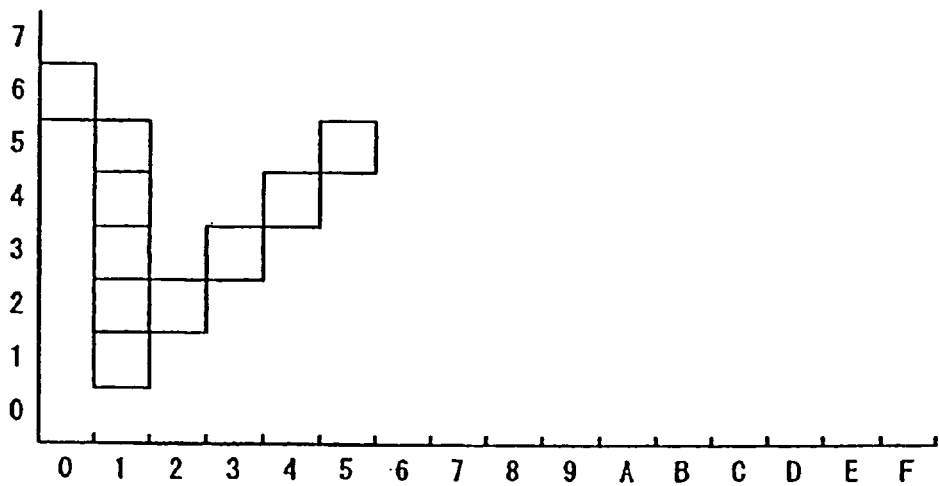

FIG. 23

| RISE MOVEMENT RATE N | RISE CLASS |
|---|---|
| N = 0 (NUMBER OF RISE TIMES=0) | 0 |
| N = 10 | 1 |
| 10 < N ≦ 11 | 2 |
| 11 < N ≦ 13 | 3 |
| 13 < N ≦ 16 | 4 |
| 16 < N | 5 |

| DROP MOVEMENT RATE M | DROP CLASS |
|---|---|
| M = 0 (NUMBER OF DROP TIMES=0) | 0 |
| M = 10 | 1 |
| 10 < M ≦ 11 | 2 |
| 11 < M ≦ 13 | 3 |
| 13 < M ≦ 16 | 4 |
| 16 < M | 5 |

VISCOSITY CLASS DETERMINATION TABLE

| | DROP CLASS | | | | | |
|---|---|---|---|---|---|---|
| | | 0 | 1 | 2 | 3 | 4 | 5 |
| RISE CLASS | 0 | 0 | 1 | 2 | 2 | 3 | 5 |
| | 1 | 1 | 1 | 3 | 4 | 5 | 6 |
| | 2 | 2 | 3 | 4 | 5 | 5 | 6 |
| | 3 | 3 | 4 | 5 | 6 | 6 | 6 |
| | 4 | 4 | 5 | 6 | 6 | 6 | 6 |
| | 5 | 6 | 6 | 6 | 6 | 6 | 6 |

FIG. 24

MOMENTUM DETERMINATION TABLE

| COMPRESSION RATE / VISCOSITY CLASS | 100% CLASS 0 | 95% OR MORE CLASS 1 | 90% OR MORE CLASS 2 | 80% OR MORE CLASS 3 | 70% OR MORE CLASS 4 | 50% OR MORE CLASS 5 | 25% OR MORE CLASS 6 | 0% OR MORE CLASS 7 |
|---|---|---|---|---|---|---|---|---|
| | AVL0 | AVL0 | AVL0 | AVL0 | AVL1 | AVL1 | AVL2 | AVL3 |
| | AVL0 | AVL0 | AVL1 | AVL1 | AVL2 | AVL3 | AVL3 | AVL4 |
| | AVL0 | AVL1 | AVL2 | AVL3 | AVL3 | AVL4 | AVL4 | AVL6 |
| | AVL0 | AVL2 | AVL3 | AVL4 | AVL4 | AVL5 | AVL5 | AVL7 |
| | AVL1 | AVL3 | AVL4 | AVL5 | AVL5 | AVL6 | AVL6 | AVL7 |
| | AVL1 | AVL4 | AVL5 | AVL6 | AVL6 | AVL7 | AVL7 | AVL7 |
| | AVL2 | AVL5 | AVL6 | AVL7 | AVL7 | AVL7 | AVL7 | AVL7 |

FIG. 26

| RAINDROP DETECTION AMOUNT IN 256 ms SECTION | WAVEFORM MOMENTUM AT ADHESION  LOWER ←――――――――――――――→ HIGHER | | | | | | | |
|---|---|---|---|---|---|---|---|---|
| | AVL0 | AVL1 | AVL2 | AVL3 | AVL4 | AVL5 | AVL6 | AVL7 |
| 0 | 0 | | | | | | | |
| 1 | 1 | 1 | 1 | 1 | 1 | 1 | 1 | 1 |
| 2 or 3 | 2 | 3 | 4 | 5 | 5 | 6 | 6 | 7 |
| 4 | 3 | 4 | 5 | 6 | 6 | 7 | 7 | 7 |

FIG. 29

● LOW-SPEED CONTINUOUS TRANSITION CONDITION

| NUMBER OF BLOCKS WITH ADHESION IN 4 BLOCKS | 0 | 1 | 2 | 3 | 4 |
|---|---|---|---|---|---|
| TOTAL POINT OF 4 BLOCKS | don't care | don't care | don't care | 15 OR MORE | 20 OR MORE |
| TRANSITION / NO TRANSITION | NO TRANSITION | NO TRANSITION | NO TRANSITION | TRANSITION | TRANSITION |

● HIGH-SPEED CONTINUOUS TRANSITION CONDITION

| NUMBER OF BLOCKS WITH ADHESION IN 4 BLOCKS | 0 | 1 | 2 | 3 | 4 |
|---|---|---|---|---|---|
| TOTAL POINT OF 4 BLOCKS | don't care | don't care | don't care | 21 OR MORE | 26 OR MORE |
| TRANSITION / NO TRANSITION | NO TRANSITION | NO TRANSITION | NO TRANSITION | TRANSITION | TRANSITION |

FIG. 30

● LOW-SPEED CONTINUOUS TRANSITION CONDITION

| NUMBER OF BLOCKS WITH ADHESION IN 4 BLOCKS | 0 | 1 | 2 | 3 | 4 |
|---|---|---|---|---|---|
| TOTAL POINT OF 4 BLOCKS | don't care | LESS THAN 2 | LESS THAN 4 | don't care | don't care |
| WITHDRAWAL / NO WITHDRAWAL | WITHDRAWAL | WITHDRAWAL | WITHDRAWAL | NO WITHDRAWAL | NO WITHDRAWAL |

● HIGH-SPEED CONTINUOUS TRANSITION CONDITION

| NUMBER OF BLOCKS WITH ADHESION IN 4 BLOCKS | 0 | 1 | 2 | 3 | 4 |
|---|---|---|---|---|---|
| TOTAL POINT OF 4 BLOCKS | don't care | LESS THAN 3 | LESS THAN 6 | LESS THAN 8 | don't care |
| WITHDRAWAL / NO WITHDRAWAL | WITHDRAWAL | WITHDRAWAL | WITHDRAWAL | WITHDRAWAL | NO WITHDRAWAL |

| | HIGH-SPEED CONTINUOUS | LOW-SPEED CONTINUOUS | B | C | D | E |
|---|---|---|---|---|---|---|
| CURRENT ZONE | 1 | 0 | 0 | 0 | 0 | 0 |

FIG. 35

DETERMINATION OF INTERMITTENCE AT EACH ZONE

| | AVL0 | AVL1 | AVL2 | AVL3 | AVL4 | AVL5 | AVL6 | AVL7 |
|---|---|---|---|---|---|---|---|---|
| ZONE B | 1.25 SECONDS | 0.6 SECONDS | 0.6 SECONDS | 0.6 SECONDS | 0.3 SECONDS | 0.3 SECONDS | 0.3 SECONDS | 0.3 SECONDS |
| ZONE C | 5 SECONDS | 2.5 SECONDS | 2.5 SECONDS | 2.5 SECONDS | 1.25 SECONDS | 1.25 SECONDS | 1.25 SECONDS | 1.25 SECONDS |
| ZONE D | 5 SECONDS | 5 SECONDS | 5 SECONDS | 5 SECONDS | 2.5 SECONDS | 2.5 SECONDS | 2.5 SECONDS | 2.5 SECONDS |
| ZONE E | 10 SECONDS | 10 SECONDS | 10 SECONDS | 10 SECONDS | 5 SECONDS | 5 SECONDS | 5 SECONDS | 5 SECONDS |

FIG. 36

| ZONE | P TIMER | P CYCLE |
|---|---|---|
| ZONE B | B1 | 1 SECOND |
|  | B2 | 1.5 SECONDS |
| ZONE C | C1 | 2 SECONDS |
|  | C2 | 4 SECONDS |
|  | C3 | 6 SECONDS |
| ZONE D | D1 | 8 SECONDS |
|  | D2 | 12 SECONDS |
| ZONE E | E | 16 SECONDS |

FIG. 37

| | P CYCLE | AVL0 | AVL1 | AVL2 | AVL3 | AVL4 | AVL5 | AVL6 | AVL7 |
|---|---|---|---|---|---|---|---|---|---|
| ZONE B | 1 SECOND | 0.6 SECONDS | 0.6 SECONDS | 0.6 SECONDS | 0 SECOND | 0 SECOND | 0 SECOND | 0 SECOND | 0 SECOND |
| | 1.5 SECONDS | 1.25 SECONDS | 0.6 SECONDS | 0.6 SECONDS | 0.6 SECONDS | 0 SECOND | 0 SECOND | 0 SECOND | 0 SECOND |
| ZONE C | 2 SECONDS | 2.5 SECONDS | 1.25 SECONDS | 1.25 SECONDS | 0.6 SECONDS | 0.6 SECONDS | 0.6 SECONDS | 0.6 SECONDS | 0.6 SECONDS |
| | 4 SECONDS | 5 SECONDS | 2.5 SECONDS | 2.5 SECONDS | 2.5 SECONDS | 1.25 SECONDS | 1.25 SECONDS | 1.25 SECONDS | 1.25 SECONDS |
| | 6 SECONDS | 5 SECONDS | 5 SECONDS | 5 SECONDS | 2.5 SECONDS | 2.5 SECONDS | 2.5 SECONDS | 2.5 SECONDS | 2.5 SECONDS |
| ZONE D | 8 SECONDS | 5 SECONDS | 5 SECONDS | 5 SECONDS | 5 SECONDS | 2.5 SECONDS | 2.5 SECONDS | 2.5 SECONDS | 2.5 SECONDS |
| | 12 SECONDS | 5 SECONDS | 5 SECONDS | 5 SECONDS | 5 SECONDS | 5 SECONDS | 5 SECONDS | 2.5 SECONDS | 2.5 SECONDS |
| ZONE E | 16 SECONDS | 10 SECONDS | 10 SECONDS | 10 SECONDS | 10 SECONDS | 5 SECONDS | 5 SECONDS | 5 SECONDS | 5 SECONDS |

WIPER CONTROL METHOD AND WIPER CONTROL DEVICE

FIELD OF THE INVENTION

The present invention relates to a wiper control method and a wiper control device which can stabilize wiping rhythm of a wiper while ensuring required wiping and smoothly respond to change of a rainfall situation.

BACKGROUND ART

A conventional wiper control device is known which injects LED light or the like to a detection surface provided on a windshield, receives its reflected light by a light receiving element and controls a wiper based on an output signal of the light receiving element. In this device, the rainfall state is estimated based on the output signal of the light receiving element, and the wiping state (continuous wiping, intermittent wiping, etc.) of the wiper is determined. For example, in JP-A-4-349053, the rainfall state is divided into 7 steps, and an intermittence time is set to each of the steps (FIG. 1).

Also, as another prior art, a method for detecting dynamic adhesion of raindrops (JP-A-2001-180447) and a method for evaluating fluctuation of an output signal of a light receiving element (JP-A-2002-277386) are presented by the inventors. Also, as conventional examples of a method for detecting raindrops, a method for detecting the raindrop in comparison with a reference value (so-called threshold value method) (JP-A-61-37560, for example) and a method for detecting raindrops by an integrated value of the light receiving element output (so-called integration method) (JP-A-4-349053, for example) are disclosed.

In the meantime, since the detection surface is provided on the windshield in these devices, an installation position of the detection surface (that is, a device) is limited by designability and visibility of the driver. That is, the device should be installed at a position different from the driver's vision. Also, the device is more preferable if the size is smaller, but it makes the design difficult. In addition to the above problems, the size of the detection surface is reduced. That is because expansion of the area for detection requires a high performance (high brightness) light emitting source or a large light-emitting energy, which increases a unit price of components.

Thus limited installation position is often located at the position where raindrops are difficult to adhere. Moreover, in proportion to the reduced detection area, adhesion probability of raindrops on the detection surface is lowered. In addition to the lowered adhesion probability, hitting of raindrops on the detection surface is changed. In concrete, the raindrops hitting is influenced by uneven raindrop density, vehicle running speed, wind direction, etc.

Because of the above reasons, even if the same rainfall situation for a driver continues, the raindrop adhesion situation on the detection surface might be changed. For example, when the raindrop density is uneven, there is a case where a large amount of raindrops adhere at one timing while no raindrop adhere at the next timing, which can cause frequent switch-over of wiping state of the wiper in a short time. Such a state that, despite the constant rainfall situation for a driver, switch-over of wiping state (particularly, waiting time of the wiper) frequents due to limitation of adhesion probability and the wiper operation is not stable is called hunting.

On the driver side, if it is determined that constant rainfall situation has been continuing, wiping at the same stable rhythm is desirable. Therefore, such switch-over of wiping state of the wiper does not fit the sense of the driver but it is bothersome.

In the meantime, in the wiper control, capability to follow rapid increase of rainfall or temporary deterioration of visibility should be ensured. For example, when a large amount of water drops adhere on the windshield temporarily due to temporary increase of rainfall or splashing of the opposite vehicle, required wiping should be performed quickly to secure the visibility. Therefore, if the switch-over of the wiping state is simply delayed, necessary wiping operation can not be obtained in some cases.

DISCLOSURE OF THE INVENTION

The present invention provides a wiper control method and a wiper control device which can smoothly respond to change of a rainfall situation by stabilizing wiping rhythm of a wiper (particularly, wiping waiting time) while ensuring required wiping.

As mentioned above, raindrop density is not even in the rainfall in the nature and the adhesion probability on the detection surface is limited to some extent. Therefore, even in the constant rainfall state, variation is generated in the adhesion cycle (adhesion interval in time) on the detection surface. In the wiper control, it is necessary to restrict such hunting caused by such variation of adhesion cycle and to stabilize wiper operation. In the meantime, in the wiper control, it is necessary to secure capability to follow temporary deterioration of visibility. For example, when a large amount of water drops temporarily adhere on the windshield due to splashing by an opposite vehicle or the like, it is necessary to quickly realize wiping with short intermittence time to secure visibility.

In order to satisfy these two necessities, the present invention uses a concept of zone control. Here, the zone means a plurality of hierarchical zones into which an adhesion cycle of a raindrop is classified. In the present invention, the intermittence time is determined by applying the detected adhesion cycle to each of the zones. A predetermined hurdle is provided when the adhesion cycle is moved from one zone to another zone so that the transition between zones is stabilized and switch-over of the intermittence time is also stabilized. Note that the zone indirectly determines the intermittence time and the zone does not equal to the intermittence time. In order to facilitate understanding of the present invention, the basic concept of the zone will be described using FIGS. 2 and 3. FIG. 2 is a conceptual diagram for explaining the configuration of the zone, and FIG. 3 is a conceptual diagram for explaining the basic zone transition.

The adhesion cycle of the raindrops on the detection surface is classified into a plurality of stepwise zones from the viewpoint of the length of the cycle. For example, as shown in FIG. 2, the entire zone is made of 5 zones from the zone A to the zone E. The zone A executing a special processing will be described later, and the zones B to E will be described here.

To each of the zones B to E, raindrop adhesion cycles (adhesion interval) with different length are allocated. For example, the adhesion cycles are allocated so that the adhesion cycle gets shorter in the order from the zone E to the higher zone B. Also, an intermittence time is allocated to each of the zones B to E. For example, the intermittence time is allocated so that the intermittence time gets shorter in the order from the zone E to the higher zone B.

In this zone structure, a concept called a current zone is used. Here, the current zone means a zone to which the current established adhesion cycle corresponds. For the intermittence time allocated to the present current zone, actual intermittence time is determined. Detailed explanation will be given later, but the intermittence time determined in the current zone is made as the basis. For example, if the current raindrop adhesion cycle corresponds to the zone C, the zone C is the current zone, and the intermittence time to be the basis is determined according to the intermittence time allocated to the zone C. In this way, the intermittence time is indirectly determined by the zone.

Such a current zone is moved vertically in accordance with the change in raindrop adhesion cycle (change of the length). That is because the intermittence time is made to correspond to the change in the raindrop adhesion cycle through the transition of the current zone. For example, in FIG. 2, when the present current zone is the zone C and the wiper is being operated with the intermittence time allocated to the zone C, if the raindrop adhesion cycle gets shorter or changes to the cycle of the B zone, the current zone is moved to the zone B. Then the actual intermittence time is determined according to the intermittence time allocated to the zone B.

Next, a transition method of the current zone will be described in concrete using FIG. 3. First, when adhesion of raindrops begins to be detected from the fair state without rainfall, the zone E becomes the current zone and the zone is moved toward the zone B as the raindrop adhesion cycle gets shorter. The transition to the shorter adhesion cycle can be made by one class. Alternatively, according to the detected adhesion cycle, intermediate zones can be skipped such as direct transition from the zone E to the zone B, for example. That is because, when the rainfall situation is changed to heavy rain, the current rainfall situation should be responded as soon as possible.

In the meantime, for transition in the direction where the adhesion cycle gets longer, the transition may be made by one class (B->C->D->E, for example). That is because in the case of decrease of rainfall, such a high responsiveness is not required. Also, the intermediate zones may be skipped at transition.

In the present invention, a condition to be a predetermined hurdle is provided in the transition of the current zone. This transition condition will be described below. The transition of current zone includes an upward transition and a downward transition. The upward transition is the transition to the side where the adhesion cycle is shorter, while the downward transition is the transition to the side where the adhesion cycle is longer.

First, it is necessary as the upward transition condition that edges should be generated plural number of times consecutively. Here, the edge means a phenomenon that an adhesion cycle shorter than the adhesion cycle of the current zone is detected. That is, when the adhesion cycle shorter than the adhesion cycle of the current zone is detected plural times consecutively, the upward transition is enabled. The upward transition may be made by one class in the step-up manner, but as mentioned above, direct transition to the zone to which the detected short adhesion cycle corresponds is more preferable.

Next, as the downward transition condition, it is necessary that the adhesion cycle of the current zone is not detected plural times consecutively. For example, if the rainfall is reduced and the adhesion cycle gets longer, the actual adhesion cycle gets longer than the adhesion cycle of the current zone. As a result, such a phenomenon occurs that the adhesion cycle of the current zone can not be detected. If this phenomenon occurs plural times consecutively, transition to a lower zone by one class is enabled.

While the adhesion cycle of the current zone is detected, the present zone is maintained. Also, when the adhesion cycle shorter than the adhesion cycle of the current zone is detected, the present zone is maintained till the upward transition condition is satisfied. By providing these transition conditions, the current zone can be maintained till the change of the rainfall situation itself is surely guaranteed, and hunting can be prevented. Also, by restricting influence by variation of the adhesion cycle, a constant adhesion cycle can be established.

The above-mentioned basic zone control method determines the intermittence time to be the basis according to the intermittence time of the current zone and performs wiping by the wiper according to this base intermittence time. Such wiping performed according to the base intermittence time is referred to as base wiping. By providing a predetermined condition for transition of the current zone, the zone transition is stabilized, the wiping waiting time by the wiper according to the zone is also stabilized, and hunting is prevented. However, according to this control method, responsiveness to temporary deterioration of visibility might be worsened.

Therefore, in the present invention, temporary wiping is performed when the above-mentioned edges are generated. In concrete, when the adhesion cycle shorter than the adhesion cycle of the current zone is detected, a temporary intermittence time is determined by the intermittence time of the zone to which the short adhesion cycle corresponds. Such a temporary intermittence time determined by generation of edges is referred to as an edge intermittence time. Then, wiping by the wiper is performed according to the edge intermittence time. The wiping performed according to such edge intermittence time is referred to as edge wiping.

The above-mentioned edge intermittence time is definitely temporary, and this is determined according to generation of edges and disappears by one or plural times of wiping. After the edge intermittence time disappears, the base intermittence time is maintained. If edges continue plural times, the edge intermittence time is determined at every generation of the edge, and when the edge generation satisfies the transition condition of the current zone, the current zone is moved to the edge generation zone, and the intermittence time which has been the edge intermittence time so far is maintained as the base intermittence time.

By performing wiping based on the edge generation in this way, temporary deterioration of the visibility can be quickly responded while preventing hunting.

Comparison between the above-mentioned base intermittence time and the edge intermittence time will be shown below. First, the zone of the base intermittence time is the current zone, while the zone of the edge intermittence zone is a higher zone. Next, the adhesion cycle of the base intermittence time is established by the transition condition to some extent, while the adhesion cycle of the edge intermittence time is a shorter and temporary adhesion cycle. Next, the duration of the base intermittence time is maintained till transition of the current zone and it is long and continues to exist after the zone transition as another length, while the duration of the edge intermittence time is temporary. The wiping by the base intermittence time is the base wiping, while the wiping by the edge wiping time is the edge wiping.

TABLE 1

| Intermittence time | Zone | Adhesion cycle | Duration | Wiping |
|---|---|---|---|---|
| Base intermittence time | Current zone | Established adhesion cycle | Till transition of the current zone | Base wiping |

TABLE 1-continued

| Intermittence time | Zone | Adhesion cycle | Duration | Wiping |
|---|---|---|---|---|
| Edge intermittence time | Higher than the current zone | Edge adhesion cycle | Temporary | Edge wiping |

BRIEF DESCRIPTION OF THE DRAWINGS

FIG. 11 is a diagram showing a configuration example of an edge registration table.

FIG. 22 is a diagram showing an example of a signal pattern when raindrops adhere on the detection surface.

FIG. 23 is a diagram for explaining a method for determining viscosity class.

FIG. 24 is a diagram showing a configuration example of a momentum determination table.

FIG. 26 is a diagram for explaining a point to determine the zone A transition condition.

FIG. 29 is a diagram showing a transition condition table to a low-speed continuous wiping zone and a transition condition table to a high-speed continuous wiping zone.

FIG. 30 is a diagram showing a withdrawal condition table from a low-speed continuous wiping zone and a withdrawal condition table from a high-speed continuous wiping zone.

FIG. 35 is a diagram showing an example of an intermittence time determination table.

FIG. 36 is a conceptual diagram for explaining the configuration of a fourth preferred embodiment.

FIG. 37 is a diagram showing an example of the intermittence time determination table.

BEST MODE FOR CARRYING-OUT OF THE INVENTION

First Preferred Embodiment

Figure 4:
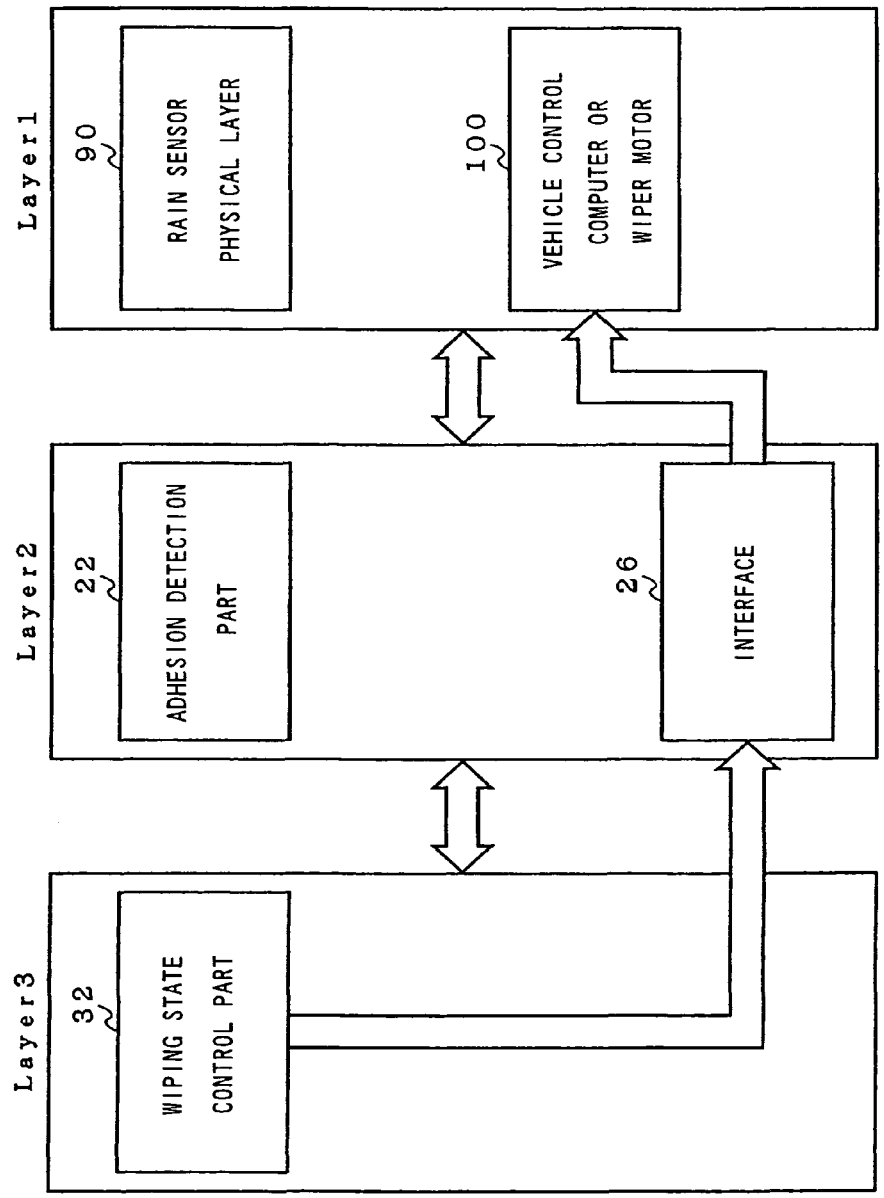
FIG. 4 is a block diagram for explaining the configuration of the wiper control device according to a first preferred embodiment of the present invention in the layered structure.

Next, the first preferred embodiment of the present invention will be described. FIG. 4 is a block diagram for explaining the construction of the wiper control device according to the first preferred embodiment of the present invention in layered structure. In FIG. 4, the wiper control device according to the first preferred embodiment of the present invention can be represented by three-layered construction, and between each of the layers, data or signals are made to communicate through a common interface such as SAP (service access point), for example. A first layer includes a rain sensor physical layer 90 and a vehicle control computer or a wiper motor 100, a second layer includes an adhesion detection part 22 and an interface 26, a third layer includes a wiping state control part 32. Each of them can be realized by software.

The rain sensor physical layer 90 is comprised by an optical mechanism and a circuit, an optical mechanism in the method that light from a light emitting element is reflected by a detection surface and a reflected light is received by a light receiving element and circuits such as a filter circuit for processing output of the light receiving element, an amplifier circuit, an A/D converter, etc., for example. An example of such a rain sensor is disclosed in the JP-A-2001-180447 and the JP-A-2002-277386.

The optical mechanism will be described. Light emitted from a light emitting element such as an LED, for example, is led to a glass substrate (windshield glass) which is a transparent substrate to detect water drops through a prism glass or the like. The led light is fully reflected by the detection surface and enters a light receiving element such as a photodiode, for example, through the above prism glass. Such an optical mechanism is arranged/constituted so that in the state where no water drop adheres, for example, the maximum output is generated at the light receiving element. At this time, if there is adhesion of a water drop or the like on the detection surface, the output of the light receiving element is lowered. Such a detection surface is arranged in the range of wiping operation of the wiper.

A vehicle control computer or wiper motor 100 is connected to the wiper control device of the present invention and can be selected as appropriate according to the preferred embodiment of the present invention. When the vehicle control computer is connected, the wiper motor is controlled through the vehicle control computer. When the wiper motor is connected, the wiper motor is directly controlled.

An adhesion detection part 22 detects adhesion of raindrops based on an output signal of the light receiving element of the rain sensor. As a method for detecting the adhesion, the method for detecting dynamic adhesion of raindrops disclosed by the inventors (JP-A-2001-180447) can be used. With this method, a delay signal is generated from a signal of the light receiving element, a difference between the signal of the light receiving element and the delay signal is acquired and it is determined that there was a collision of a rain drop on the detection surface when the difference occurs. Alternatively, a first delay signal of the signal of the light receiving element is generated, a second delay signal is generated from the first delay signal, a difference between the first delay signal and the second delay signal is acquired and when the difference occurs, it is determined that there was a collision of a rain drop on the detection surface. By this method, dynamic adhesion itself of raindrops or the like can be captured.

Therefore, the adhesion detection part 22 detects the phenomenon of collision of the raindrops on the detection surface and outputs it as adhesion of raindrops. Also, as a method for detecting adhesion, a method for detecting raindrops by comparison with a reference value (so-called threshold value method) disclosed in the JP-A-61-37560 and a method for detecting raindrops from an integrated value of light receiving element output (so-called integration method) disclosed in the JP-A-4-349053 can be used.

The interface 26 converts and outputs a wiper driving signal from the higher layer (third layer) to a signal in the format suitable for the vehicle control computer or wiper motor, respectively.

The wiping state control part 32 controls wiping state of the wiper based on the output of the adhesion detection part 22. The wiper wiping stage includes, for example, a stop state, an intermittent wiping state, a low-speed continuous wiping state and a high-speed continuous wiping state. The wiper wiping state is defined by the wiping waiting time and wiping speed. The wiping waiting time includes no waiting time. The wiping state control part 32 determines these wiping states and outputs a wiper driving signal of a predetermined wiping waiting time and a predetermined wiping speed. The wiper driving signals is outputted to the vehicle control computer or wiper motor 100 through the interface 26.

Figure 5:
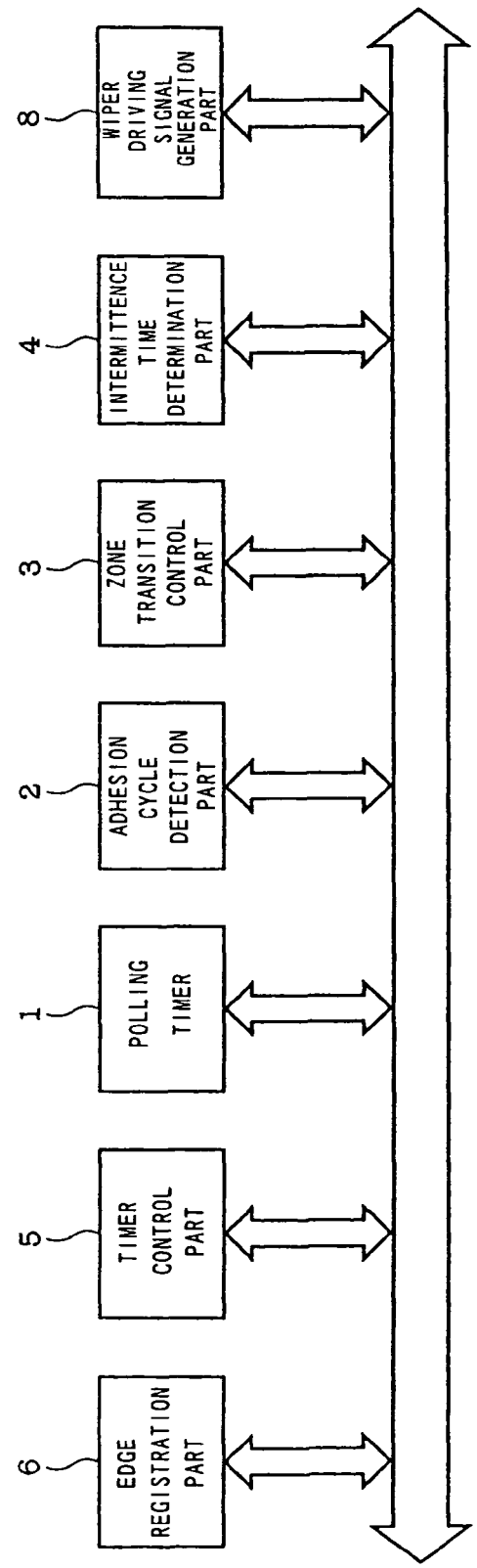
FIG. 5 is a block diagram showing the configuration of a wiping state control part.

Next, the wiping state control part 32 will be described in more detail. FIG. 5 is a block diagram showing the configuration of the wiping state control part, FIG. 6 is a block diagram for explaining the configuration of a polling timer, and FIG. 7 is a conceptual diagram for explaining a polling cycle.

As shown in FIG. 5, the wiping state control part includes a polling timer (hereinafter referred to as "P timer") 1, an adhesion cycle detection part 2, a zone transition control part 3, an intermittence time determination part 4, a timer control part 5, edge registration part 6, and a wiper driving signal generation part 8.

Figure 6:
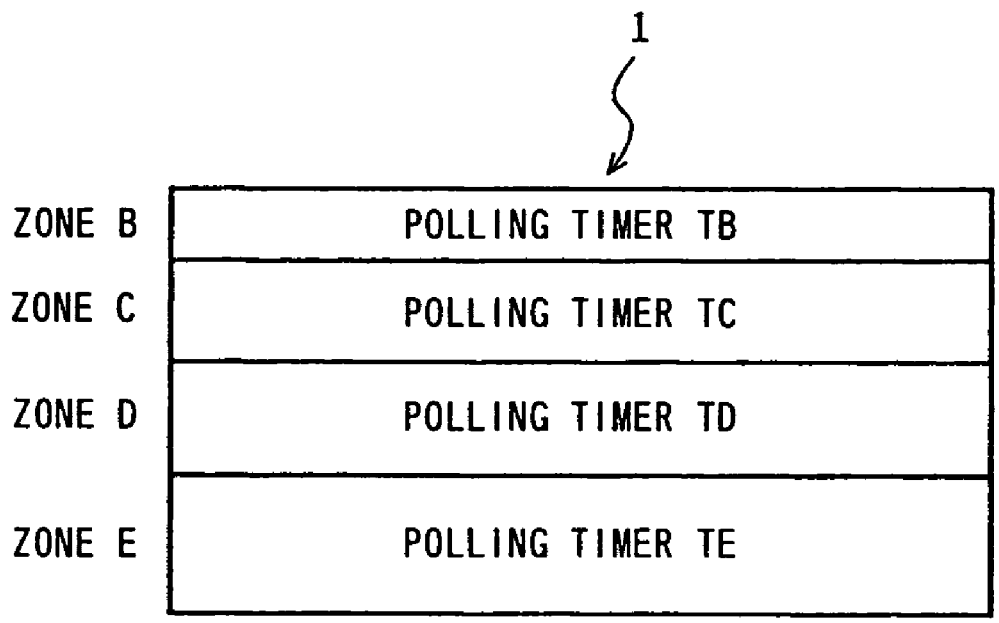
FIG. 6 is a block diagram for explaining the configuration of a polling timer.
Figure 7:
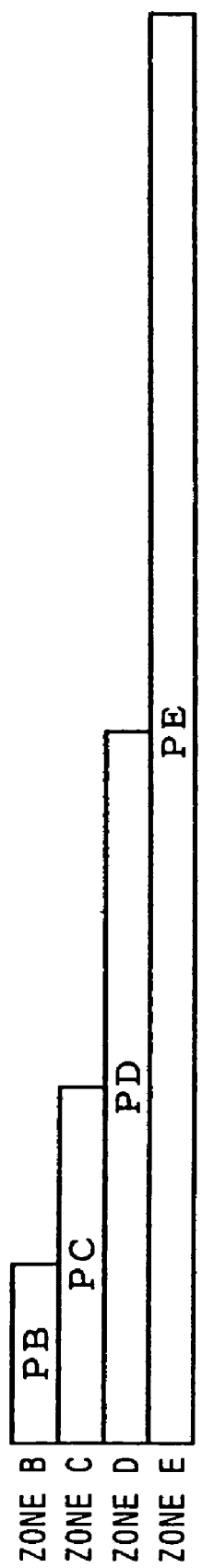
FIG. 7 is a conceptual diagram for explaining a polling cycle.

First, the P timer 1 is provided at each zone as shown in FIG. 6. The P timers in zones B to E are represented as TB to TE. Each of the P timers has a different specific polling cycle (hereinafter referred to as "P cycle)". The P cycle in the zones B to E are represented by PB to PE. As shown in FIG. 7, each of the P timers in the zones B to E (TB to TE) has a different P cycle, and the P cycle becomes longer from PB to PE. As an example, PB:PC:PD:PE=1:2:4:8.

This P timer 1 times out at every specific P cycle. With this specific P cycle as a reference, which will be described later, it is determined to which zone the adhesion cycle corresponds. Also, by timeout of this timer, timing for determining the intermittence time is supplied.

Figure 8:
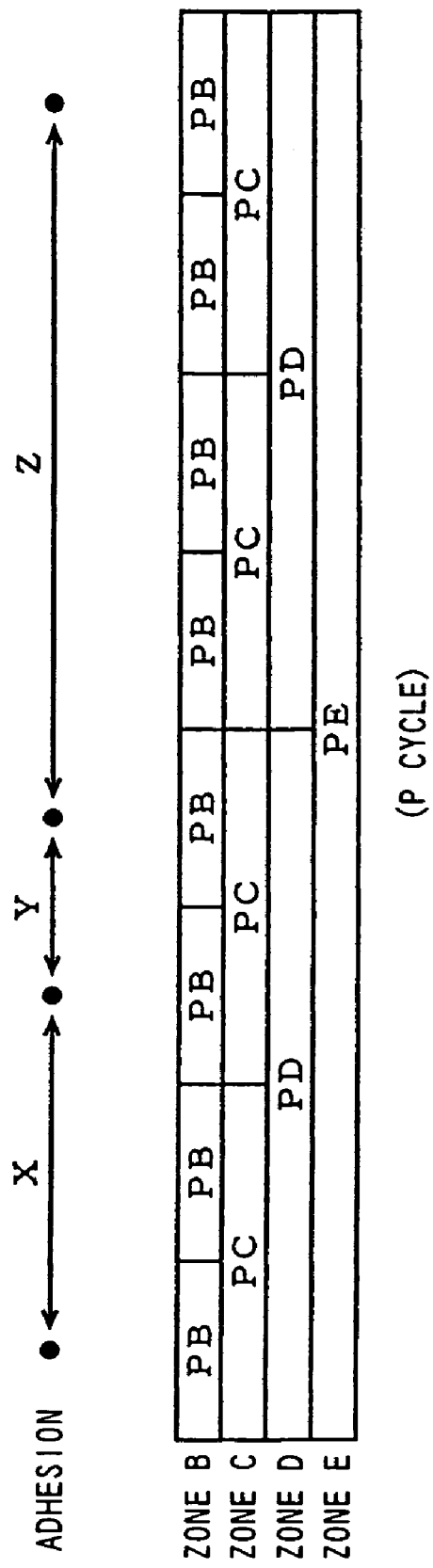
FIG. 8 is a conceptual diagram for explaining detection of the adhesion cycle.

Next, the adhesion cycle detection part 2 will be described. The adhesion cycle detection part 2 identifies the current adhesion cycle based on the output of the adhesion detection part 22. With the P cycle of each zone being as a reference, it is determined to which zone the identified current adhesion cycle corresponds. Concrete explanation will be given using FIG. 8. FIG. 8 is a conceptual diagram for explaining detection of the adhesion cycle.

If there is adhesion of raindrops with three different types of interval as shown in FIG. 8, first, the adhesion cycle X is identified. With the P cycle of each zone as a reference, it is determined that, for example, this adhesion cycle X corresponds to the P cycle PC of the zone C and falls under the zone C. The adhesion cycle Y is identified by the next adhesion. With the P cycle of each zone as a reference, it is determined that this adhesion cycle Y corresponds to the P cycle PB of the zone B and falls under the zone B. The adhesion cycle Z is identified by the next adhesion, and it is similarly determined that this adhesion cycle Z corresponds to the P cycle PD of the zone D and falls under the zone D. The adhesion cycle detection part 2 may register the P cycle and the zone to which the current adhesion cycle corresponds in the memory and manage its history. Alternatively, the registration contents may be updated at each determination of the adhesion cycle.

Figure 9:
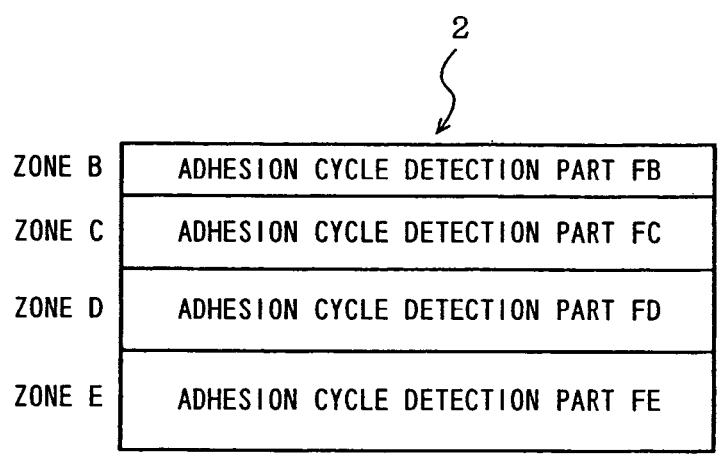
FIG. 9 is a block diagram for explaining the configuration of an adhesion cycle detection part.

Also, the adhesion cycle detection part 2 may be provided per zone as shown in FIG. 9. In this case, each of the adhesion cycle detection parts 2 may determine the adhesion cycle based only on the P cycle of its own zone and output information indicating the zone to which the current adhesion cycle corresponds (flag, for example) only when the adhesion cycle corresponds to its own P cycle. FIG. 9 is a block diagram for explaining the configuration of the adhesion cycle detection part.

Next, a method for determining the adhesion cycle will be described. The adhesion cycle may be determined with the detected adhesion of raindrops as a reference, but it is preferable that a predetermined unit section for adhesion determination is provided to construct an adhesion cycle by defining the phenomenon that adhesion of one drop or more of raindrops is detected in this unit section as a single adhesion. The adhesion cycle may be determined based on an interval between the unit sections in which adhesion of raindrops is detected.

Figure 10:
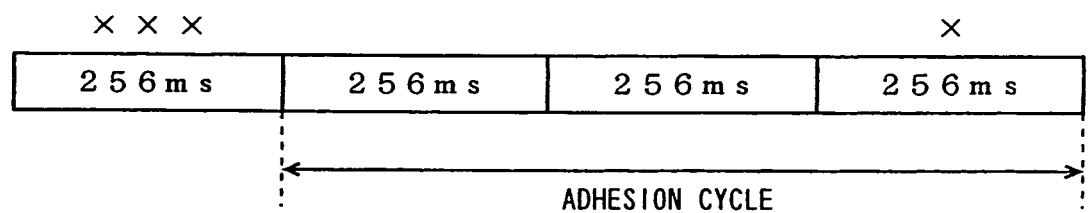
FIG. 10 is a diagram showing a method for determining an adhesion cycle of raindrops.

The method for determining the adhesion cycle of the raindrops is shown in FIG. 10. In this Fig., three drops of adhesion is detected in the first unit section, and a single drop of adhesion is detected in the fourth unit section. Therefore, one adhesion is determined in the first unit section and one adhesion is determined in the fourth unit section. The adhesion cycle is determined by the interval between the first unit section and the fourth unit section. In this method, even if plural adhesions of raindrops are detected in the unit section, it is considered as one adhesion. Also, the unit section for determining adhesion is to determine the minimum adhesion cycle.

Such configuration was made according to the following reasons. In the case of rain with high density, for example, an actual adhesion cycle of the raindrop adhering on the detection surface can be as short as several tens of ms. Also, when a raindrop with a large diameter hits the detection surface and water drops with a small diameter are splashed, a large number of small water drops can adhere at the same time. If such a short adhesion cycle is used as it is for control, behavior of the wiper might become unstable.

The predetermined unit section for such adhesion determination is preferably determined considering stability and responsiveness of the wiper behavior. If the unit section is set long, for example, the stability of the wiper is improved, while responsiveness is lowered. If it is set short, on the contrary, the responsiveness is improved but stability is lowered and processing load is increased. The unit section thus determined is 256 ms, for example.

Next, the edge registration part 6 will be described. The edge registration part 6 detects generation of an edge based on the output of the adhesion cycle detection part 2 and registers the edge in the memory. For example, the latest adhesion cycle zone determined by the adhesion cycle detection part 2 is compared with the current zone, and if the latest adhesion cycle zone is higher than the current zone, the generation of an edge is detected, and data of the generation of the edge and the higher zone where the edge was generated are registered. In other words, the phenomenon that an adhesion cycle shorter than the adhesion cycle of the current zone was detected and the zone where the phenomenon was generated are registered.

Figure 11:
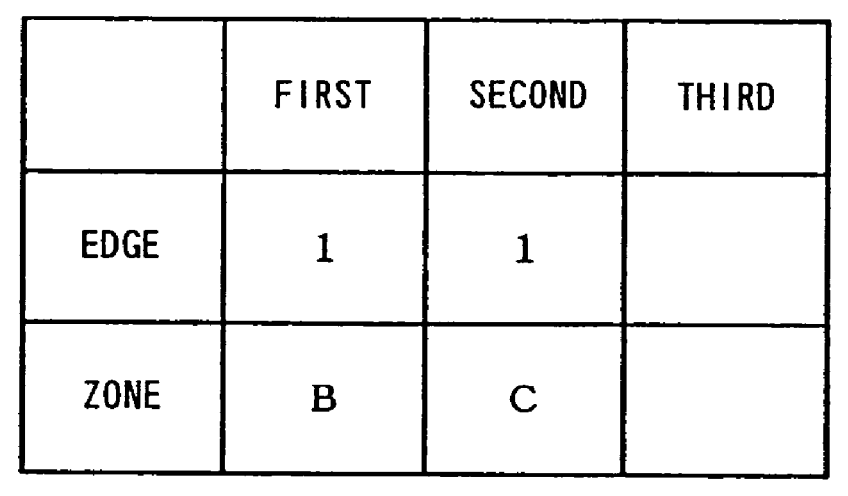

FIG. 11 shows a configuration example of the edge registration table. As shown in FIG. 11, the edge generation information and the zone where the edge was generated are registered in the edge registration table. If the edge is consecutively generated, the information is accumulated. As will be described later, based on the phenomenon that the P timer of the current zone times out, the edge registration part 6 clears all the registered edges. Also, when there is a transition of zones, the edge registration part 6 also clears all the registered edges.

Next, the timer control part 5 will be described. As mentioned above, each of the polling timers 1 has its own P cycle and times out at each of its P cycle. The timer control part 5 resets a predetermined P timer in a predetermined case. In concrete, when an edge is generated in a zone higher than the current zone, all the P timers in the zones lower than the zone where the edge was generated (including the current zone) are reset. Such reset is made because the start axis of adhesion cycle determination is matched by resetting the P timers.

Figure 12:
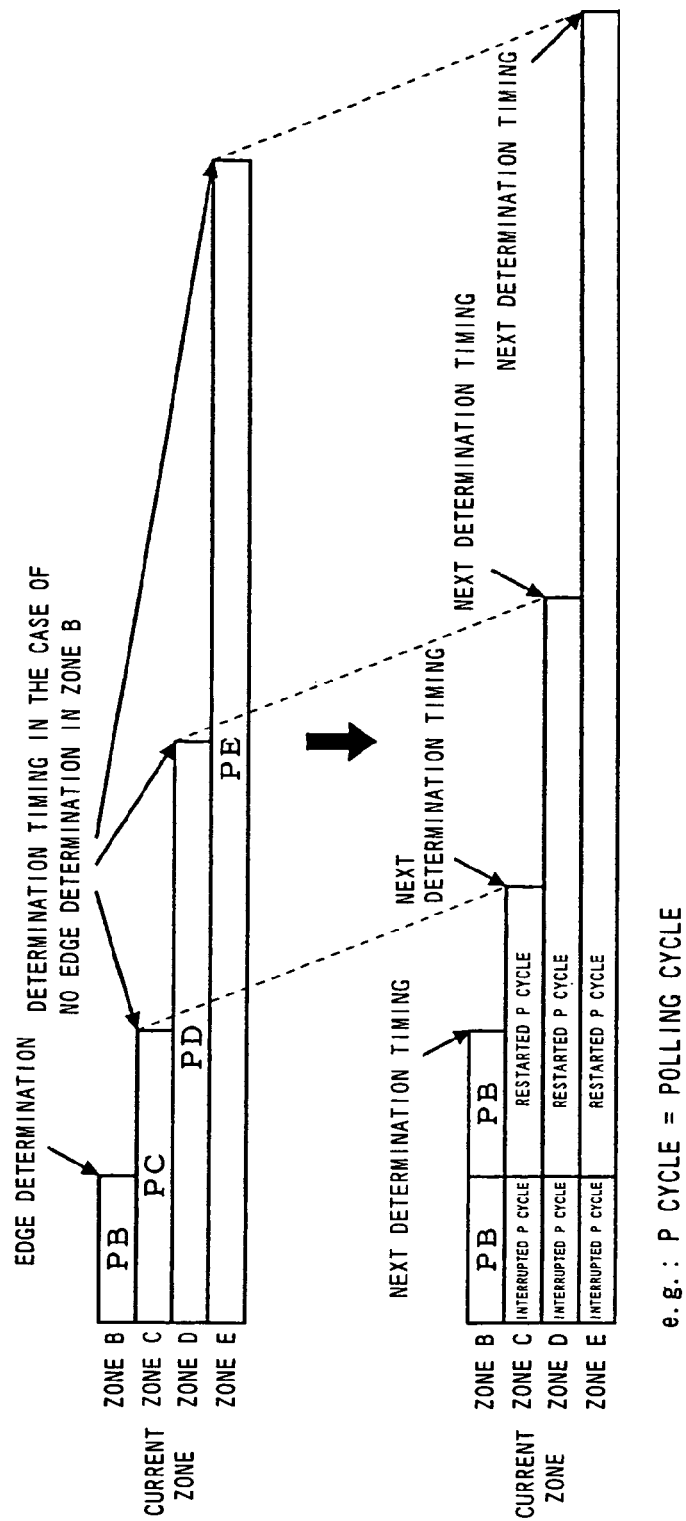
FIG. 12 is a diagram showing a relation between edge generation and P timer reset.

The relation between the edge generation and the P timer reset is shown in FIG. 12. In FIG. 12, suppose such a case that an edge is generated in the higher zone B if the current zone is the zone C, for example, is shown. In this case, the timer control part 5 resets all the lower P timers at timeout of the P cycle of the zone B where the edge was generated and they are restarted. By this, the P cycles in the zones C and below are interrupted, and all the P cycles are restated at a unified start axis.

For example, the timer control part 5 is started by generation of an edge or registration of an edge and identifies the zone where the edge was generated referring to the edge registration table. All the P timers in the edge zone and below may be reset at the timing of the first timeout of the P timer of the zone where the edge was generated.

Next, the zone transition control part 3 will be described. The zone transition control part 3 determines the first current zone at start of rainfall and controls transition of the current zone according to a predetermined condition. The predetermined transition conditions are shown below. As shown in Table 2, upward transition is enabled if edges are generated a predetermined consecutive number of times. If the adhesion cycle of the current zone is not detected a predetermined consecutive number of times, the downward transition is enabled. In the meantime, the present current zone is maintained in the other cases.

TABLE 2

| Upward transition | Consecutive generation of edges a predetermined number of times |
| --- | --- |
| Downward transition | Adhesion cycle of the current zone is not detected consecutively a predetermined number of times |
| Maintenance of the present state | The other cases |

Figure 13:
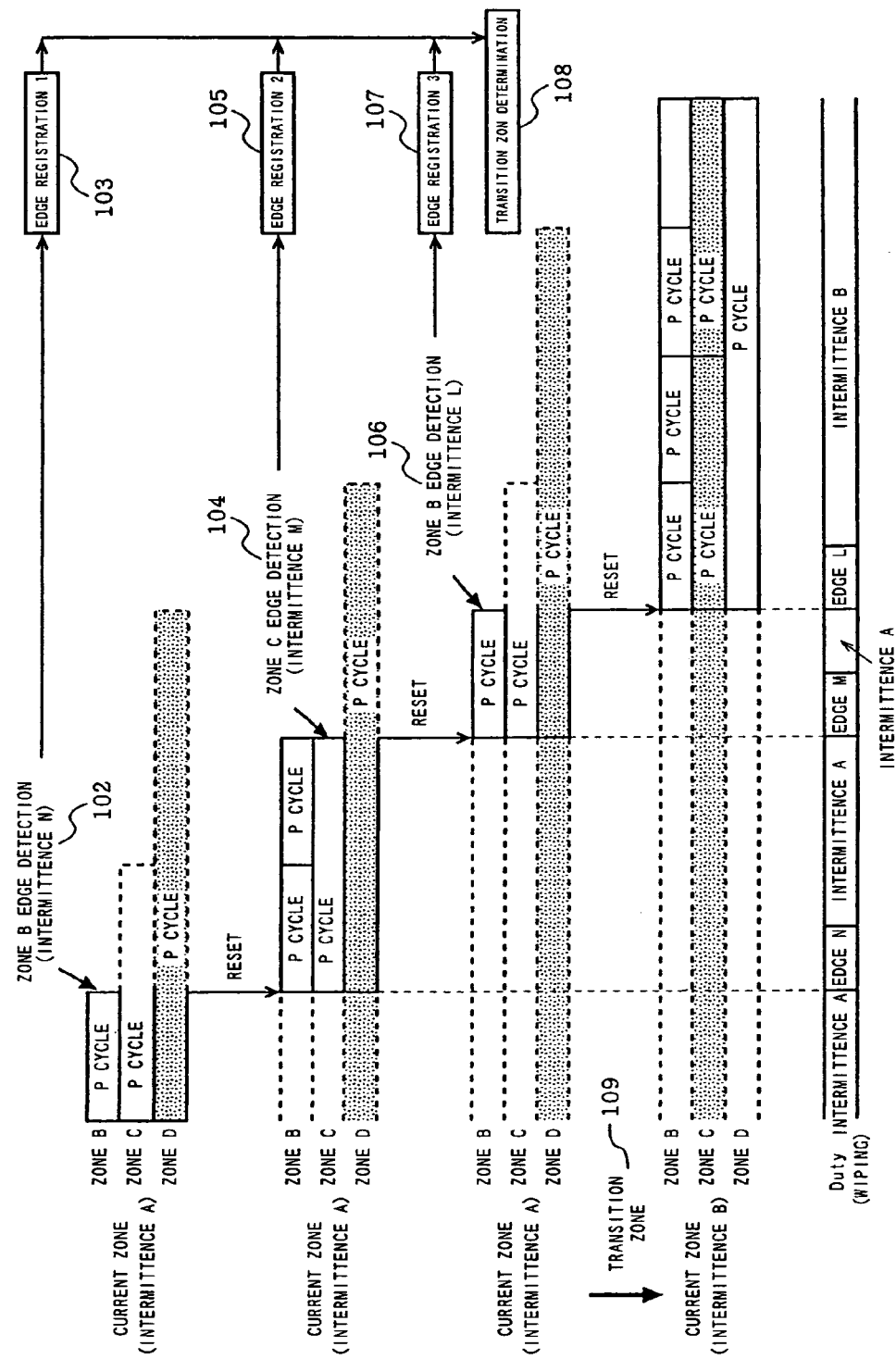
FIG. 13 is a conceptual diagram showing an example of upward transition.

The upward transition will be described. FIG. 13 is a conceptual diagram showing an example of the upward transition. In FIG. 13, suppose that the current zone is the zone D. First, an edge is detected in the zone B (102), the timers in the zone C and below are reset and the edge and the zone are registered (103). Next, the edge is detected in the zone C (104), the timers in the zone D and below are reset and the edge and the zone are registered (105). And the edge is detected again in the zone B (106), the timers in the zone C and below are reset, and the edge and the zone are registered (107).

Figures 14, 15, 16:
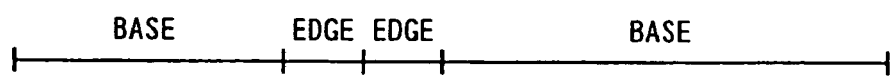
FIG. 14 is a diagram showing an example of the edge registration table in which edges are registered three consecutive times.
FIG. 15 is a diagram showing an example of a current zone table.
FIG. 16 is a diagram showing an example of an output of an intermittence time determination part 4.

An example of the edge registration table in which the edges are registered three consecutive times is shown in FIG. 14. In this way, by the phenomenon that the edges are registered a predetermined number of times consecutively (three times, here), the zone transition control part 3 determines the zone for transition (108). The determination of the transition zone may be made, for example, by acquiring an average value of the adhesion cycles of the three times of edges and selecting the zone proximate to this average value. The transition zone is determined and the current zone is changed from the zone D to the zone C (109). The determination of the transition zone may be started by the timing of timeout of the P timer in the zone where the edge satisfying the transition condition (third edge, here) is generated.

FIG. 15 shows an example of the current zone table. The zone transition control part 3 manages the current zone table as shown in FIG. 15, for example, and updates the current zone table at every transition of the zone.

Next, the downward transition will be described. The condition for the downward transition is that, for a predetermined consecutive number of times (condition 1), the adhesion cycle of the current zone cannot be detected (condition 2). The zone transition control part 3 determines if these conditions are met or not, and if met, it executes processing to lower the current zone lower by one class.

In concrete, this processing is executed as follows. First, the base of this predetermined number of times is the P cycle of the current zone. That is, the timing when the P timer of the current zone times out makes a single time. Therefore, when the P timer of the current zone times out a predetermined number of times consecutively, the above condition 1 is satisfied.

Next, the fact that the adhesion cycle of the current zone cannot be detected (condition 2) means that adhesion cannot be detected in the P cycle of the current zone. Therefore, the condition of the downward transition that, for a predetermined consecutive number of times (condition 1), the adhesion cycle of the current zone can not be detected (condition 2) is satisfied when the P timer of the current zone times out a predetermined number of times consecutively and there is no adhesion during that period.

As concrete control, for example, the zone transition control part 3 is started at the timing when the P timer of the current zone times out and determines if the P timer of the current zone times out a predetermined number of times consecutively. In order to make such determination, it is preferable to integrate the number of timeout times of a current timer. This integrated number of timeout times may be cleared by generation of an edge.

When the P timer of the current zone times out a predetermined consecutive number of times, the zone transition control part 3 determines if adhesion was detected or not during the P cycle in the predetermined number of times. If no adhesion was detected, the current zone is moved lower by one class and the current zone table as shown in FIG. 15 is updated. In order to make such control, the corresponding P cycle may be associated with each adhesion and the history of adhesion is stored.

On the other hand, if adhesion is detected during the predetermined number of times, the present current zone is maintained. And at the next timeout of the P timer of the current zone, similar processing is executed again. At the next determination, the P cycle of the targeted predetermined number is shifted by one P cycle to be the latest one.

An example of the predetermined number of times in the upward transition condition and the predetermined number of times in the downward transition condition is shown in Table 3. As shown in Table 3, the predetermined number of times in the upward transition may be set with a different value for each zone. Alternatively a single time may be set as the predetermined number of times. This predetermined number of times determines easiness of transition and the larger the value of the number of times is, the higher the transition hurdle becomes. This also applies to the downward transition.

TABLE 3

|  | Upward transition | Downward transition |
| --- | --- | --- |
| Zone B | 3 | 4 |
| Zone C | 2 | 3 |
| Zone D | 1 | 2 |
| Zone E | 1 | 1 |

Next, the intermittence time determination part 4 will be described. The intermittence time determination part 4 determines the intermittence time to drive the wiper. Two types of intermittence time are determined: the above-mentioned base intermittence time and the edge intermittence time. The intermittence time determination part 4 determines an actual intermittence time (base intermittence time) for the intermittence time allocated to the current zone in principle. However, in case of edge generation, the actual intermittence time (edge intermittence time) is temporarily determined for the intermittence time allocated to the zone where the edge was generated, and this edge intermittence time is maintained for a predetermined period of time or predetermined number of wiping times. When this predetermined period of time or predetermined number of wiping times is finished, the object is returned to the intermittence time of the current zone.

FIG. 16 shows an example of an output of the intermittence time determination part 4. The intermittence time determination part 4 outputs the above base intermittence time and the edge intermittence time serially, and the intermittence time as output is such that the base intermittence time and the edge intermittence time are sequentially aligned on a single time axis as shown in FIG. 16. Based on the intermittence time outputted in this way, the wiper driving signal generation part 8 outputs a wiper driving signal of a predetermined wiping waiting time and a predetermined wiping speed.

To be more concrete, as represented as Duty in FIG. 13, first, the base intermittence time of the current zone (intermittence A) is outputted and then, the edge intermittence time (edge N) is outputted by detection of an edge in the zone B. After that, returning to the current zone and the intermittence A is outputted, an edge M is outputted by detection of an edge in the zone C, and after returning to the current zone, the intermittence A is outputted. Next, by detection of an edge in the zone B, an edge L is outputted, the current zone is moved to the zone C and an intermittence B is outputted.

The intermittence time determination part 4 will be described in more detail. The intermittence time determination part 4 is started by timeout of the P timer. The intermittence time determination part 4 is started by the timeout of the P timer of the current zone and the timeout of the P timer of the zone where an edge was generated. In this preferred embodiment, the P timer of the current zone is reset and will not time out in the situation where an edge is generated, and timeout of either timer is automatically selected depending on presence of generation of an edge.

When the P timer of the current zone times out, the intermittence time determination part 4 determines the intermittence time for the intermittence time allocated to the current zone. The intermittence time to be determined may be one or plural. On the other hand, if the P timer of the zone where an edge is generated times out, the intermittence time determination part 4 determines the intermittence time for the intermittence time allocated to the zone where the edge was generated. In this case, too, the intermittence time to be determined may be one or plural.

Figure 17:
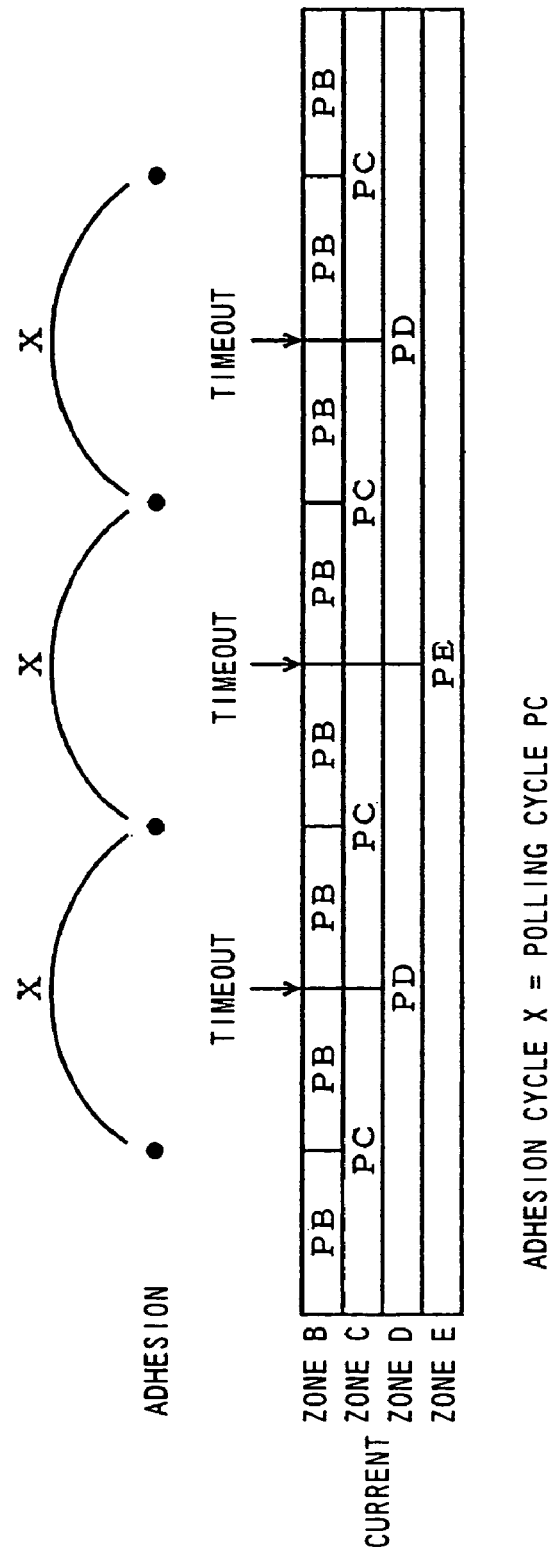
FIG. 17 is a conceptual diagram for explaining a relation between the adhesion cycle and determination of intermittence time.
Figure 18:
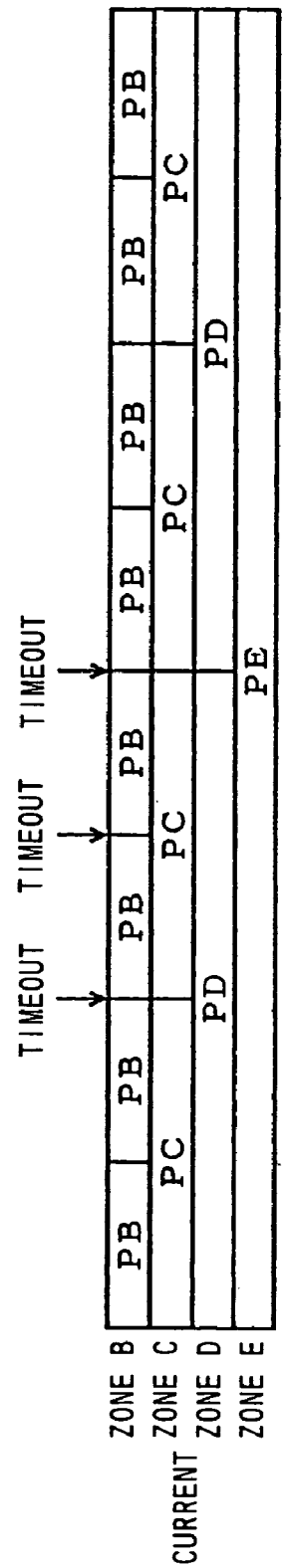
FIG. 18 is a conceptual diagram for explaining a relation between the adhesion cycle and determination of intermittence time.

Next, the relation between the adhesion cycle and determination of intermittence time will be described using FIGS. 17 and 18. FIGS. 17 and 18 are conceptual diagrams for explaining the relation between the adhesion cycle and determination of the intermittence time. In FIG. 17, the current zone is the zone C, and a raindrop adhesion cycle X was detected. Here, suppose that the raindrop adhesion cycle X corresponds to the polling cycle PC.

In this case, the adhesion cycle detection part 2 determines that the current adhesion cycle corresponds to the zone C, and the adhesion cycle of the zone C is detected. Next, the intermittence time determination part 4 determines the intermittence time at the timing of timeout of the polling timer of the current zone. The target intermittence time is the intermittence time allocated to the current zone. In the case of FIG. 17, the intermittence time allocated to the zone C, which is the current zone at the timing of PC timeout is determined as the actual intermittence time.

Next, the case of edge wiping will be described using FIG. 18. In FIG. 18, the current zone is the zone C, and the raindrop adhesion cycle Y shorter than X was detected. Here, suppose that the raindrop adhesion cycle Y corresponds to the polling cycle PB.

In this case, the adhesion cycle detection part 2 determines that the current adhesion cycle corresponds to the zone B, and the adhesion cycle of the zone B is detected. By this, the edge registration part 6 detects generation of an edge and registers it in the memory. Next, the intermittence time determination part 4 determines the intermittence time at the timing of timeout of the polling timer of the zone B where the edge was generated. The target intermittence time is the intermittence time allocated to the zone B where the edge was generated. In the case of FIG. 18, the intermittence time allocated to the zone B at the timing of PB timeout is determined as the actual intermittence time.

Operation of the First Preferred Embodiment

Figure 19:
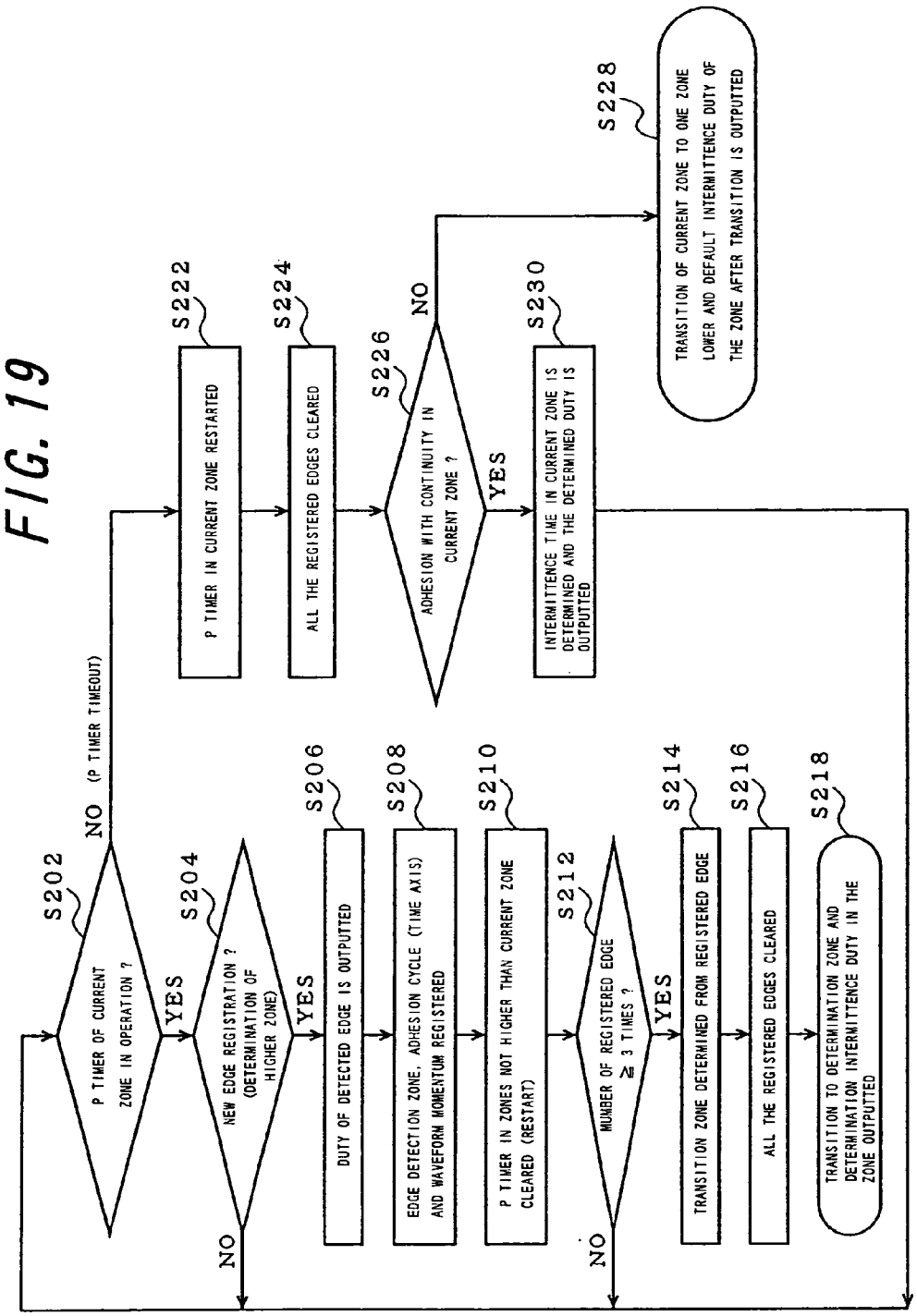
FIG. 19 is a flowchart for explaining entire operation of the first preferred embodiment.

Next, the entire operation of the above first preferred embodiment will be described using FIG. 19. Here, FIG. 19 is a flowchart for explaining the entire operation of the first preferred embodiment. At Step 202, first, it is determined if the P timer in the current zone is in operation or not. If the P timer is in operation, it means that the P timer in the current zone does not time out. Therefore, at Step 204, it is determined if a new edge is registered or not, and if no new edge is registered, the routine returns to Step 202.

In the meantime, if a new edge was registered, at Step 206, the edge wiping of the intermittence time determined by the zone where the edge was generated is outputted. At Step 208, the edge generation zone, adhesion cycle, waveform momentum, etc. are registered. The waveform momentum will be described later. Next, at Step 210, the P timer in the zone lower than the edge generation zone is reset and restarted.

Next, at Step 212, it is determined if the number of accumulated edge registrations is three or not, and if less than three, the routine returns to Step 202. In the meantime, if the number of accumulated edge registrations reaches 3 times, a zone to be moved is determined at Step 214, and all the registered edges are cleared at Step 216. Next, at Step 218, the current zone is moved to a new zone, and the base wiping is outputted according to the intermittence time of the current zone after transition.

In the meantime, if it is determined that the P timer in the current zone has timed out at Step 202, the P timer in the current zone is restarted at Step 222, and all the registered edges are cleared at Step 224.

Next, at Step 226, it is determined if adhesion can not detected in the current zone for a predetermined consecutive number of times and if the adhesion can not be detected for the predetermined consecutive number of times, the current zone is moved lower by one class at step 228, and the base wiping is outputted according to the intermittence time of the current zone after transition. In the meantime, if the condition is not met at step 226, the intermittence time is determined for the intermittence time allocated to the present current zone at Step 230, and the base wiping is outputted according to the determined intermittence time and the routine returns to Step 202.

By this, in the first preferred embodiment of the present invention, temporary deterioration of visibility can be smoothly responded while preventing hunting of the intermittence caused by variation of adhesion cycles.

Second Preferred Embodiment

Next, a second preferred embodiment will be described. By the intermittence time control method shown in the first preferred embodiment, temporary deterioration of visibility can be responded while preventing hunting. In the meantime, the rainfall situation can rapidly change in the nature. Particularly, in the case of rapid heavy rain, immediate responsiveness is demanded for the wiper operation in order to secure visibility quickly. On the other hand, in the case of rapid drizzling rain, immediateness is not so much required. Also, in the case of the heavy rain, not the intermittence wiping but so-called continuous wiping is required. The difference between the intermittence wiping and the continuous wiping is that the continuous wiping does not have wiper waiting time.

Figures 1, 2:
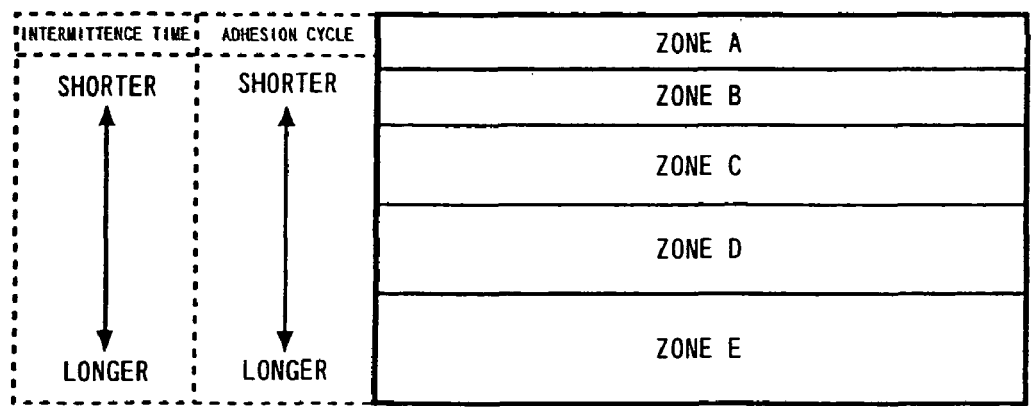
FIG. 1 is a diagram for explaining the conventional wiper control method.
FIG. 2 is a conceptual diagram for explaining the zone configuration.
Figure 3:
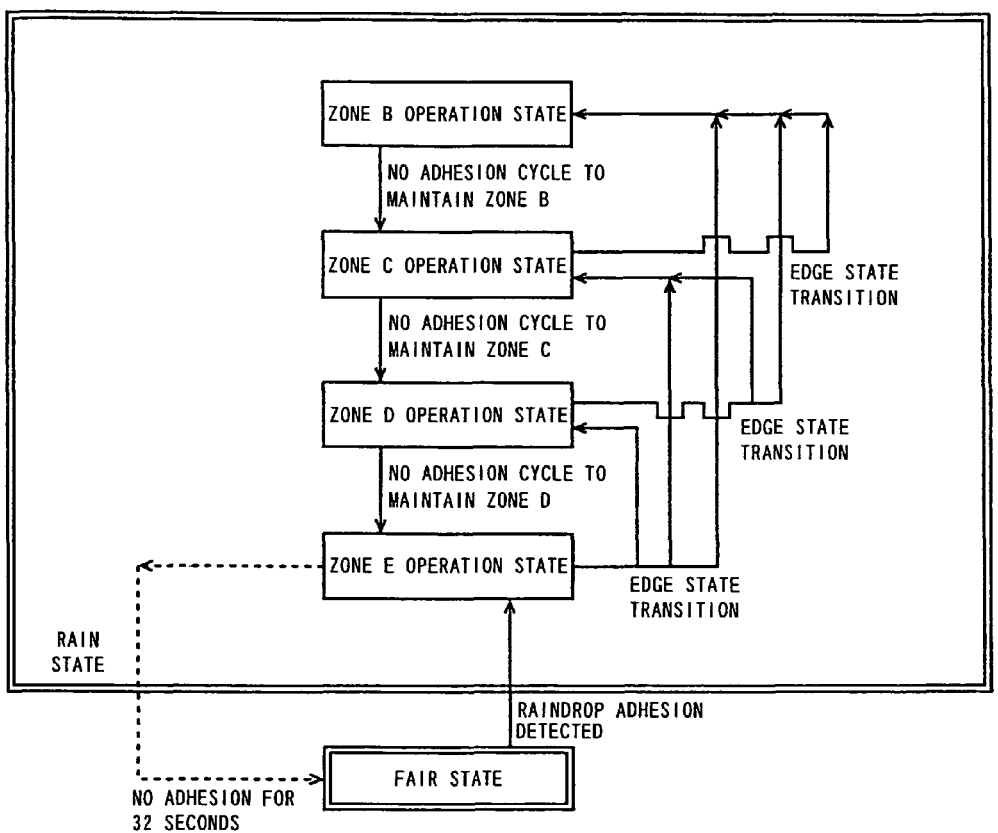
FIG. 3 is a conceptual diagram for explaining basic transition of the zone.

The second preferred embodiment of the present invention is to realize continuous wiping quickly when the rainfall situation is rapidly changed to heavy rain. In concrete, this is realized by providing the zone A shown in FIG. 2. The zone A will be described. First, to the zone A, continuous wiping with waiting time zero, not the intermittence time, is allocated. To this continuous wiping, plural types of wiping speeds such as high speed and low speed, for example, may be set. Therefore, the zone A may be subdivided into a high-speed continuous wiping zone and a low-speed continuous wiping zone. And in this preferred embodiment, when the current zone is moved to the zone A, one of the continuous wiping types is outputted.

Figure 20:
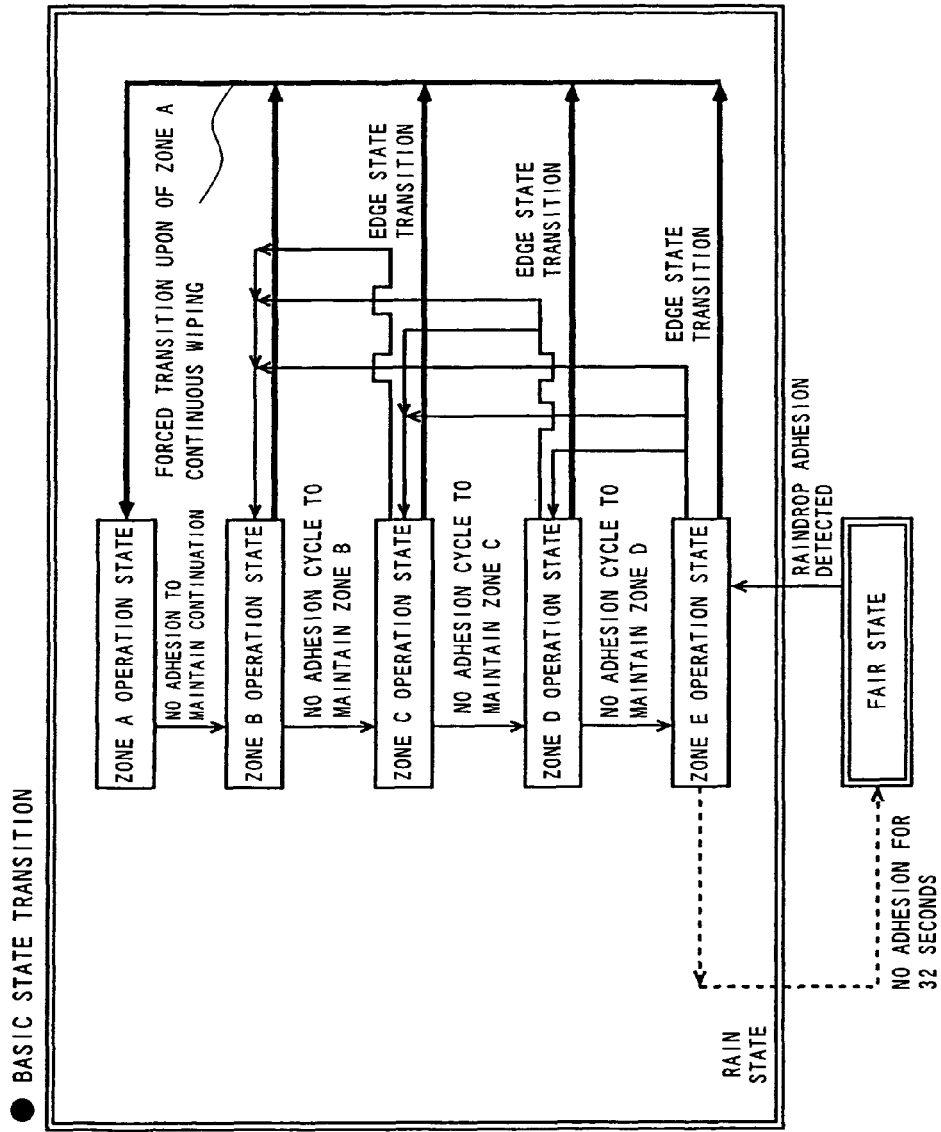
FIG. 20 is a conceptual diagram for explaining the zone transition of a second preferred embodiment.

FIG. 20 is a conceptual diagram for explaining transition of the zone of the second preferred embodiment. In FIG. 20, the transition to the zone A can be made from any of the lower zones B to E. In concrete, if a situation requiring continuous wiping is detected according to a predetermined transition condition, transition is made to the zone A all the time. In the meantime, in the case of downward transition from the zone A, the transition is made lower by one class. Based on the consideration by the inventors, the situation requiring continuous wiping can be represented by two conditions: that adhesion continues to some extent (condition 1) and that the momentum of the adhering raindrop is large (condition 2).

Figure 21:
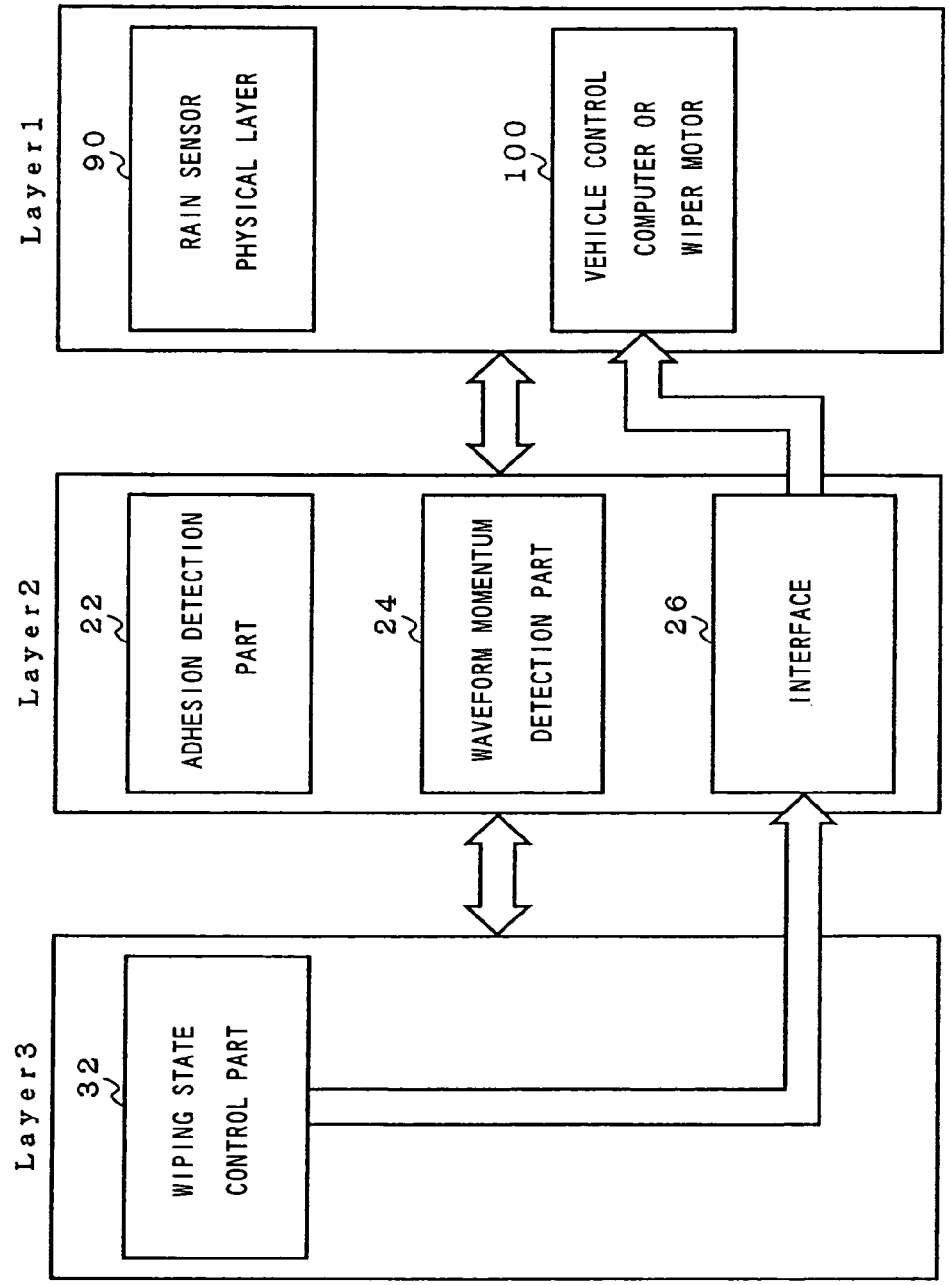
FIG. 21 is a block diagram for explaining the configuration of the wiper control device according to the second preferred embodiment of the present invention in the layered structure.
Figure 25:
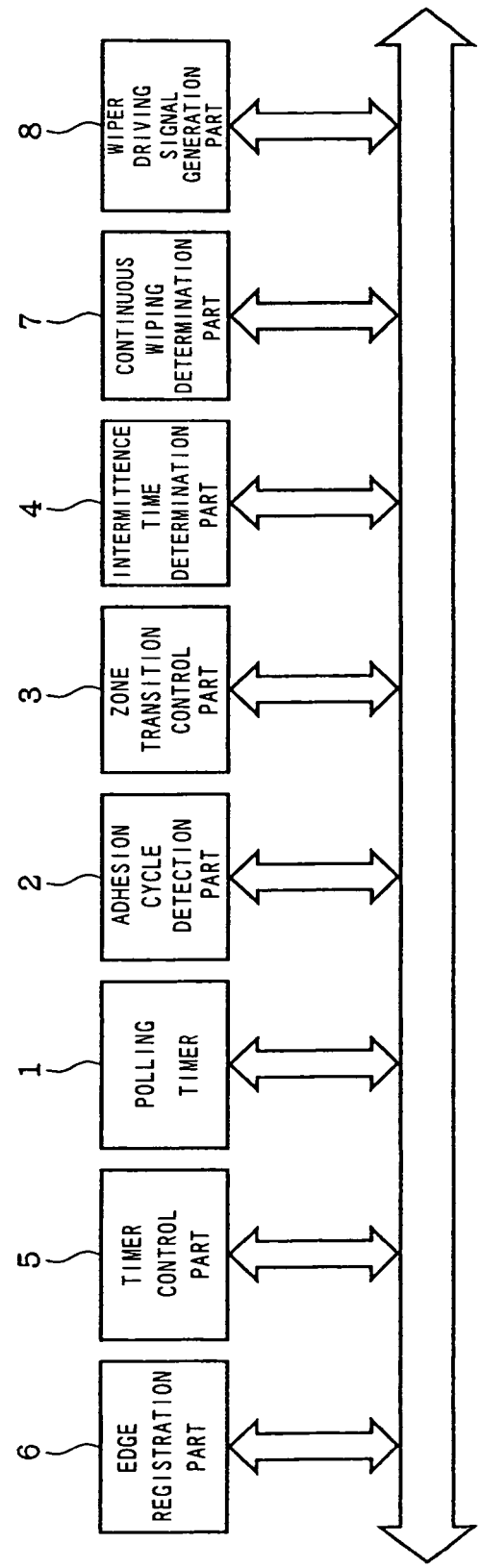
FIG. 25 is a diagram showing the configuration of the wiping state control part according to the second preferred embodiment.

FIG. 21 is a block diagram for explaining the configuration of the wiper control device according to the second preferred embodiment of the present invention in the layered structure. In FIG. 21, the difference from the first preferred embodiment is that the second layer includes a waveform momentum detection part 24. This waveform momentum detection part 24 has a function to detect the momentum of a raindrop appearing on the waveform of an output signal of a light receiving element when the raindrop adheres to the detection surface. This raindrop momentum is in proportion to the size of the adhering raindrop and the intensity of the raindrop when it collides with the windshield. Therefore, by this waveform momentum, the size of the raindrop, the intensity of the raindrop hitting, etc. can be estimated.

(Waveform Momentum)

Here, the waveform momentum will be described. In JP-A-2002-277386 disclosed by the inventors, a method which can indirectly detect dynamic fluctuation of an adhering object by dynamic fluctuation of a signal of a light receiving element obtained through the raindrops adhering on the detection surface and moreover can determine the size of raindrop and the intensity of raindrop hitting by the change pattern of the fluctuation the signal.

The change pattern of the signal fluctuation used in the above determination can be a change pattern of the time of fluctuation of the above signal, and the length of the fluctuation of the adhering object by the length of the signal fluctuation. For example, if the adhering object is a raindrop, as its physical characteristic, the larger the raindrop is, the longer the fluctuation lasts, and the size of the raindrop can be estimated from the length of the detected fluctuation.

Also, the change pattern of the signal fluctuation used in the above determination can be a change pattern of the size of the fluctuation of the above signal, and the size of the fluctuation of the adhering object can be indirectly detected by the size of the signal fluctuation. For example, if the adhering object is a raindrop, as its physical characteristic, the larger the raindrop is, the larger the fluctuation is, and the size of the raindrop can be estimated from the size of the detected fluctuation. Parameters representing the size of the fluctuation include the number of change times of increase/decrease in the fluctuation, the change amount of the increase and the direction of increase/decrease of the change.

In the present invention, the waveform momentum is acquired from such fluctuation of a signal of the light receiving element.

A concrete method for acquiring a waveform momentum will be shown below.

(Segmentation Processing)

FIG. 22(A) is a typical example of a signal pattern when a raindrop adheres on the detection surface. First, prior to pattern recognition processing, a segment was provided for a signal value. Each segment is preferably given a label code.

Next, in a matrix of a signal-value axis and a time axis, a block (tile) defined by each segment is assumed. Pattern recognition processing is executed using a block through which an inputted signal pattern passes.

(Change Pattern of Length of the Signal Fluctuation)

Data compression and calculation of compression rate as a means for evaluating the length of the signal fluctuation will be described in concrete.

If the segments passed by the inputted signal pattern continue in the direction of the time axis, the subsequent segment is stacked on the first segment. This can be understood as the tiles continuing in the same segment are stacked on the first tile. In this way, in the signal arrangement, if there is a portion where signals belonging to the same segment continue, those continuing signals are compressed. FIG. 22(B) shows a diagram modeling this.

For example, in this Fig., the sampling signals which occupied 16 segments on the time axis are compressed to the sampling signals over 6 segments.

Next, a method for acquiring a compression rate will be described.

In the signal pattern in FIG. 22(A), as mentioned above, the sampling signals over 16 segments on the time axis are compressed to the sampling signals over 6 segments.

Here, the phenomenon at adhesion of a raindrop will be considered. At the moment when a raindrop adheres, a rapid decrease of a signal is observed.

Then, with the rapid signal decrease as the start of an event, compression may be considered within a predetermined time thereafter. For example, in the case of FIG. 22, if the predetermined time is a period of 15 segments from 1 to F, it is compressed to the sampling signals over 5 segments. That is, the compression rate is (15−5)/15=0.67.

The relation between the compression rate and the size of the raindrop will be described. When a large raindrop adheres on the detection surface, a time is required till the motion is completed, and the signal compression rate is relatively small. On the other hand, in the case of a small raindrop, the time till the motion is completed is short, and the signal compression rate is relatively large. For example, the compression rate is 100% in the fair weather, and the heavier the rain becomes, the larger the compression rate drops.

(Change Pattern of the Size of Signal Fluctuation after Adhesion)

Next, as a means for evaluating the change pattern of the size of signal fluctuation, detection of the number of change times of the signal extending over plural segments and calculation of displacement amount in the upward or downward direction of the change will be described in concrete.

As shown in FIG. 22(A), the input signal has its signal value increased by 1 segment from the sampling signal of the preceding segment in the sampling segments of the sixth, seventh, eighth and Eth segments on the time axis. That is, the number of changes of the signal value over plural segments is 4 and the displacement amount is increase of 4 segments. Also, the direction of rise/drop of the change is only rise of 4 times.

In this way, in the fluctuation of the output signal of the light receiving element, any change in the rise direction or drop direction over plural segments is defined as a change.

That is, even if the waveform is raised or lowered, when it does not extend over plural segments, it is not considered as a change. Also, the number of rising segments or dropping segments in 1 segment on the time axis is determined as the displacement amount.

In the signal waveform, the large number of change times over segments of a signal value leads to an estimation of a large raindrop, while the small number of change times to a small raindrop.

In the displacement amount, a large rise leads to an estimation of a large raindrop, while a small rise to a small raindrop.

In the configuration that the number of change times of a signal at adhesion and after adhesion is acquired, it is not necessary to separately acquire the number of segments of the sampling signals compressed in the above data compression.

That is, the signal drop at the adhesion is included in the number of change times, and the sum with the number of change times of the signal after adhesion corresponds to the number of segments of the sampling signals after compression. A unit time for evaluating an event of adhesion of a single raindrop is set. An expression to acquire the compression rate with the number of sample segments on the time axis in the unit time as S is shown below:

$$\text{Compression rate} = \{S - (\text{number of rises} + \text{number of drops})\} \times 100/S \quad \text{[Expression 1]}$$

Also, to acquire the waveform momentum, the rise movement rate and drop movement rate of the waveform in the above-mentioned unit time are calculated. The total number of changes in the rise direction is set as the number of rise times and the total number of changes in the drop direction as the number of drop times. Then the total of the displacement amounts in the rise direction is set as the total rise displacement amount, while the total of the displacement amount in the drop direction is set as the total drop displacement amount. Expressions to acquire the rise movement rate and the drop movement rate are shown below:

$$\text{Rise movement rate} = (\text{total rise displacement amount} \times 10)/\text{number of rise times}$$

$$\text{Drop movement rate} = (\text{total drop displacement amount} \times 10)/\text{number of drop times} \quad \text{[Expression 2]}$$

Next, the fluctuation of raindrops will be evaluated based on the above-mentioned rise movement rate and drop movement rate. There, based on the rise movement rate and the drop movement rate, the raindrop fluctuation is classified by the unit of viscosity. The viscosity is the unit to represent the size of fluctuation determined considering the rise movement rate and the drop movement rate. FIG. 23 shows a method for determining the viscosity class.

As shown in FIG. 23, a rise class is acquired from the rise movement rate N, while a drop class is acquired from the drop movement rate M. The viscosity class is determined by a viscosity class determination table comprised by a matrix of the rise class axis and the drop class axis.

Next, the waveform momentum is acquired from the above acquired compression rate and the viscosity class. FIG. 24 shows a configuration example of the momentum determination table. As shown in FIG. 24, the momentum determination table is comprised by a matrix of the viscosity class axis and the compression rate axis. At the intersection between the viscosity class and the compression rate, a value of the momentum is arranged. In this example, the momentum is represented by AVL, and the value of AVL is in proportion to the size of the raindrop momentum. By referring to such a table, the waveform momentum can be acquired.

The waveform momentum detection part 24 acquires the compression rate of the waveform of an adhering raindrop and the rise movement rate and the drop movement rate from the waveform of an output signal of the light receiving element as mentioned above. Next, using the rise movement rate and the drop movement rate, the viscosity class is acquired referring to the viscosity class determination table. Next, using the compression rate and the viscosity class and referring to the momentum determination table, the momentum of the adhering raindrop is acquired and outputted. Such a momentum may be outputted every detection of raindrop adhesion.

(Continuous Wiping Determination Part)

The configuration of the wiping state control part according to the second preferred embodiment is shown in FIG. 24. The difference from the above-mentioned first preferred embodiment is addition of the continuous wiping determination part 7. Since the other constitutional elements are the same as in the first preferred embodiment, detailed description will be omitted. The continuous wiping determination part 7 determines if the transition condition to the zone A is met or not based on the number of adhesions in a predetermined time and the waveform momentum at the adhesion. If the transition condition is met, the current zone is forced to move to the zone A, and the continuous wiping is outputted. Then the current zone table is updated to the zone A. According to this outputted continuous wiping, the wiper driving signal generation part 8 continuously generates a wiper driving signal.

(Method for Determining Zone A Transition Condition)

Next, the method for determining zone A transition condition will be described. First, for a sample for evaluating adhesion of a raindrop, a unit section is set on the time axis. This unit section may be determined as appropriate from a required response time of the wiper. For example, the longer the unit section is set, the longer the time to obtain a sample required for determination of zone A transition becomes, and the response time also gets longer. On the other hand, if the unit section is made too small, load of calculation processing would become too large. An example of the unit section thus determined is 256 ms, for example.

Figure 27:
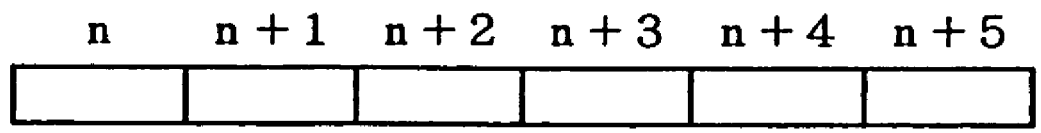
FIG. 27 is a diagram for explaining a point to determine the zone A transition condition.

On the other hand, as shown in FIG. 26, a matrix table comprised by the number of adhesions in the unit section and the waveform momentum at the adhesion is registered in the memory. The continuous wiping determination part 7 acquires a point in the unit section by applying the number of adhesions in the unit section and the waveform momentum at the adhesion outputted from the second layer to the matrix table. If the number of adhesions in the unit section is plural, a value of the momentum to be used (AVL value) may be a representative value or an average value. FIGS. 26 and 27 are diagrams for explaining the point to determine the zone A transition condition.

Next, an identification number (n, for example) is given to the sample section and the point is stored in the memory. The point is acquired similarly for the next unit section, and the next identification number (n+1) is given and stored in the memory. The points for each unit section are sequentially stored in the memory in this way. If the unit section is represented by a single block, the blocks are aligned in the time series as in FIG. 27.

Figure 28:
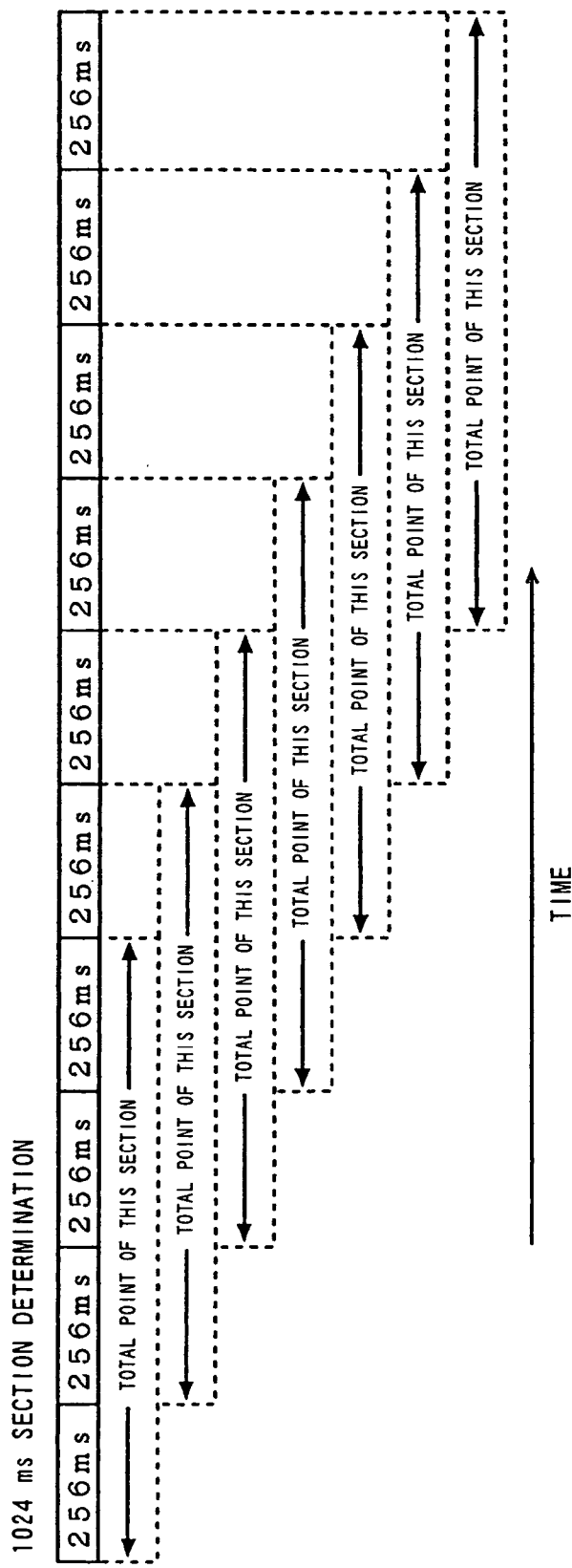
FIG. 28 is a conceptual diagram for explaining a method for determining the zone A transition condition.

Next, the continuous wiping determination part 7 determines the transition condition for a predetermined number (4, for example) of consecutive blocks from the blocks aligned in the time series. The targeted block may be updated by shifting 1 block at each determination as shown in FIG. 28. FIG. 28 is a conceptual diagram for explaining the method for determining the zone A transition condition.

FIG. 29 shows a transition condition table to a low-speed continuous wiping zone and a condition table of transition to a high-speed continuous wiping table, and FIG. 30 shows a withdrawal condition table from the low-speed continuous wiping zone and a condition table of withdrawal from the high-speed continuous wiping zone. The continuous wiping determination part 7 acquires the number of blocks with adhesion from the targeted 4 blocks. Then, the point values of the targeted 4 blocks are summed. Using this number of blocks with adhesion and the point total value, referring to the transition condition table as in FIG. 29, it is determined if transition should be made to any of the continuous wiping zone. If the condition is met, the current zone is moved to the zone concerned.

Next, if the current zone is in any of the continuous wiping zones, the continuous wiping determination part 7 determines if withdrawal should be made from the present continuous wiping zone or not using the number of blocks with adhesion and the point total value and referring to the withdrawal condition table as in FIG. 30. If the condition is met, the current zone is moved to a zone lower by one class.

Figures 31, 32:
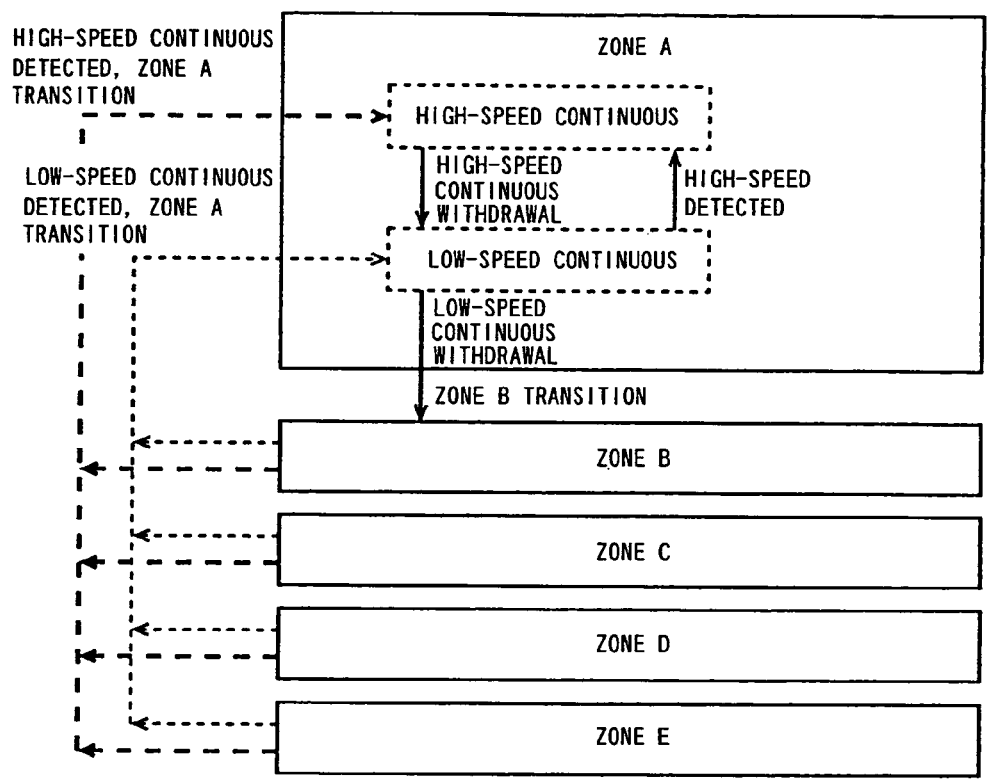
FIG. 31 is a conceptual diagram for explaining the zone transition of the second preferred embodiment.
FIG. 32 is a diagram for explaining the configuration example of the current zone table.

Next, an example of zone transition will be described. FIG. 31 is a conceptual diagram for explaining the zone transition of the second preferred embodiment, and FIG. 32 is a diagram for explaining the configuration example of the current zone table. In this FIG. 31, the continuous wiping zone (zone A) further includes a high-speed continuous wiping zone and a low-speed continuous wiping zone.

The current zone is determined independently by the zone transition control part 3. When a transition condition of a high-speed or a low-speed is detected, the continuous wiping determination part 7 forces transition of the current zone to the applicable continuous wiping zone taking priority over the determination of the zone transition control part 3. Then, the current zone table as in FIG. 32 is updated to the applicable zone.

For example, if transition is made from the zone C to the low-speed continuous wiping zone, the continuous wiping determination part 7 updates the current zone table from the zone C to the low-speed continuous wiping zone. Next, when the withdrawal condition to the low-speed continuous wiping zone is detected, the continuous wiping determination part 7 moves the current zone to the zone B, one class lower, and updates the current zone table from the low-speed continuous wiping zone to the zone B. Based on the occurrence of this phenomenon, transition of the current zone is controlled by the zone transition control part 3.

On the other hand, when the transition condition of the high-speed continuous wiping is detected, the continuous wiping determination part 7 moves the current zone to the high-speed continuous wiping zone and updates the current zone table to the high-speed continuous wiping zone. Next, if the high-speed continuous wiping zone is the current zone, the continuous wiping determination part 7 moves the current zone to the low-speed continuous wiping zone upon detection of the withdrawal condition, and in the low-speed continuous wiping zone, the operation is the same as mentioned above.

Figure 33:
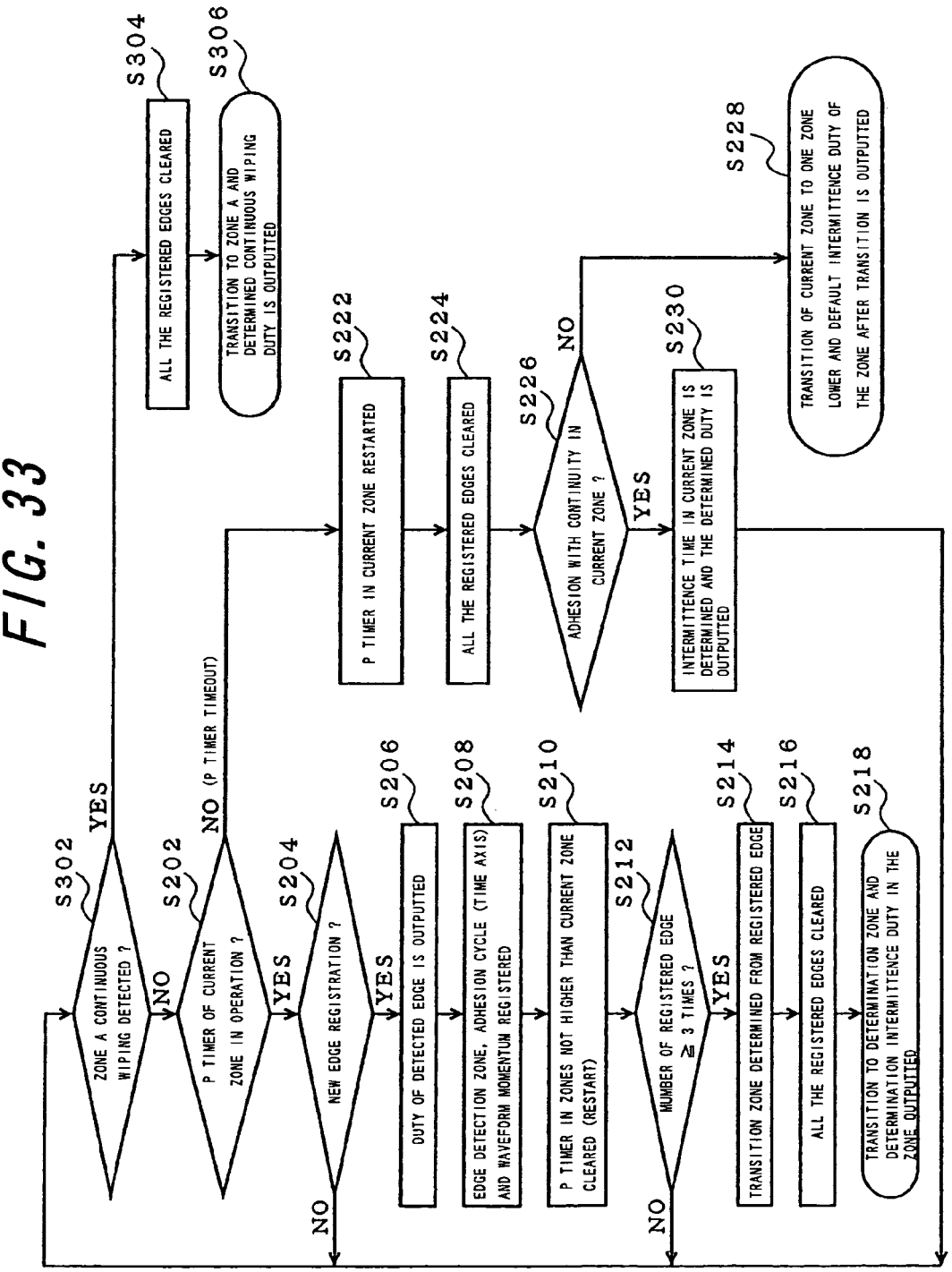
FIG. 33 is a flowchart for explaining operation of the second preferred embodiment.

Next, the operation of the above-mentioned second preferred embodiment will be described using FIG. 33. Here, FIG. 33 is a flowchart for explaining the operation of the second preferred embodiment. In this flowchart of FIG. 33, the same steps as those in the flowchart of FIG. 19 are given the same numerals and their description will be omitted.

First, the loop from Steps 204, 212 and 230 returns to Step 302. And at Step 302, it is determined if the transition condition of the zone A is detected. If the transition condition is not detected, the routine goes to Step 202 and the same processing as in the first preferred embodiment is executed.

On the other hand, if the transition condition of the zone A is detected at Step 302, all the registered edges are cleared at Step 304, and transition is made to the zone A at Step 306 and a predetermined continuous wiping is outputted.

By constituting in this way, even if the wiper is operating in the intermittent state, the continuous wiping state can be realized quickly at a point of time when a required condition is detected.

(Forced Edge Wiping)

The above mentioned example is configured so that the continuous wiping determination part 7 determines transition to the zone A. In addition, it may be so constituted that the continuous wiping determination part 7 determines forced edge wiping. Here, the forced edge wiping is the wiping with zero waiting time and the wiping in which a delay can not be generated by a delay element such as a sensitivity volume. Such forced edge wiping is useful in the situation that emergency wiping is required to avoid risk or the like. Also, the forced edge wiping may include a high-speed edge wiping and a low-speed edge wiping. The high-speed edge wiping and the low-speed edge wiping can be realized by varying the wiping speed.

In concrete, the continuous wiping determination part 7 determines forced edge wiping for consecutive blocks in the number smaller than that used for determination of the transition condition (2, for example) from the blocks aligned in the time series as shown in FIG. 27. As a concrete determination method, a matrix with point values of each of the two blocks as an axis, necessity of the forced edge wiping is determined. If the forced edge wiping is necessary, before determining the transition condition to the zone A, the forced edge wiping is determined and outputted. Also, the high-speed edge wiping and the low-speed edge wiping can be determined using a matrix with the point values of each of the above 2 blocks as an axis.

By constituting in this way, wiping required while transition to the zone A is being determined can be also responded, and a predetermined time for determination can be given to the transition to the zone A, and hunting in the transition to the zone A can be prevented.

Also, by making determination using 2 blocks with the unit section of 256 ms, a forced edge wiping signal can be outputted in almost 0.5 second, and wiping by the wiper can be realized in about 1 second. Here, 1 second is an average time required for a driver to operate the wiper at emergency.

Third Preferred Embodiment

Next, the third preferred embodiment of the present invention will be described. In the above preferred embodiments, description was made supposing that the intermittence time allocated to each of the zones is 1 for convenience. If the diameters of all the raindrops are the same, it is only necessary to determine the intermittence time based only on the adhesion cycle. However, based on the consideration by the inventors, it was confirmed that the diameters of raindrops in the nature are varied, and the larger the diameter becomes, the more easily the visibility is interfered in a short time. Therefore, even with the same adhesion cycle, it is preferable that wiping is performed in a shorter time if the diameter of the raindrops is large. The third preferred embodiment of the present invention satisfies such a necessity.

In the third preferred embodiment of the present invention, a plurality of intermittence times are allocated to each zone and an appropriate intermittence time is selected from the plural intermittence times according to the diameter of the adhering raindrop. In concrete, the size of the adhering raindrop is distinguished based on the above-mentioned waveform momentum of the raindrop, and the intermittence time is determined according to the distinguished raindrop size.

Figure 34:
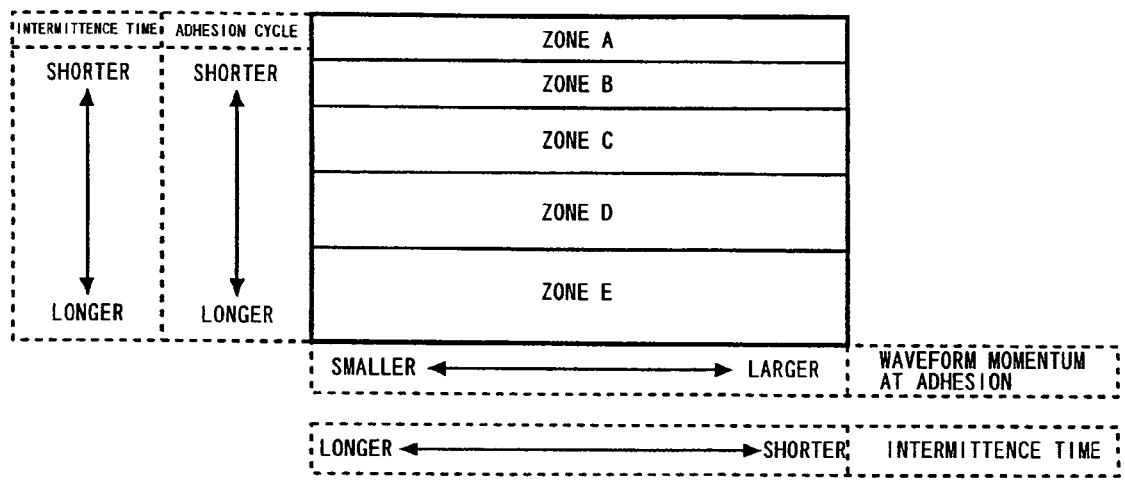
FIG. 34 is a conceptual diagram for explaining the zone configuration of a third preferred embodiment.

The third preferred embodiment of the present invention will be described using FIG. 34. FIG. 34 is a conceptual diagram for explaining the configuration of the zone according to the third preferred embodiment. As shown in FIG. 34, in the third preferred embodiment, the waveform momentum at adhesion is set on the horizontal axis. The intermittence time is set so that the wiper waiting time gets shorter in reverse proportion to the waveform momentum.

The present invention uses such combination of the waveform momentum and the adhesion cycle. In concrete, in the present invention, the current zone and the edge zone are determined based on the adhesion cycle. From a plurality of intermittence times allocated to the current zone and the edge zone, an appropriate intermittence time is determined based on the waveform momentum.

The third preferred embodiment will be described more concretely. FIG. 35 shows an example of an intermittence time determination table. This table is comprised by a matrix of a zone axis and a momentum axis.

The intermittence time determination part 4 determines the intermittence time referring to this intermittence time determination table. In concrete, the zone for determination of the intermittence time (current zone or the edge generation zone) and the momentum of the detected adhesion are obtained, and the intermittence time is determined referring to the intermittence time determination table. To execute such control, it is preferable that the adhesion cycle detection part 2 stores the waveform momentum in the memory as a history for each adhesion, for example. The intermittence time determination part 4 can obtain the waveform momentum referring to the history of such adhesion.

When an edge is generated, the edge registration part 6 preferably registers the waveform momentum at the edge generation in the edge registration table. The intermittence time determination part 4 may determine the edge intermittence time from the waveform momentum at the edge generation.

By combining the adhesion cycle and the raindrop size (waveform momentum) in this way, the rainfall situation can be categorized in more detail. Also, an appropriate intermittence time can be set for individual rainfall situation thus categorized. Therefore, more appropriate wiper operation can be realized for rainfall situation.

Fourth Preferred Embodiment

Next, a fourth preferred embodiment of the present invention will be described. In the above preferred embodiments, such an example was described that a single P timer is provided in each zone, and the P cycle in each zone is single. In the fourth preferred embodiment of the present invention, an example of provision of a plurality of P timers in 1 zone will be described.

The fourth preferred embodiment will be described concretely using FIG. 36. FIG. 36 is a conceptual diagram for explaining the configuration of the fourth preferred embodiment. What is characteristic in FIG. 36 is that a plurality of P timers are provided in each zone, and each of the P timers has subdivided specific adhesion cycle allocated. The P cycle in this Fig. is set, as in the above first preferred embodiment, so that the P cycle gets longer sequentially from the zone B to the zone E.

The characteristic in the fourth preferred embodiment is that the adhesion cycle is determined in more detail, and the intermittence time is set in more detail. In concrete, the actual intermittence time in each zone is determined by a plurality of adhesion cycles and waveform momentum. In other words, the adhesion cycle is divided more finely than in the above-mentioned third preferred embodiment to categorize the rainfall situation in more detail.

The fourth preferred embodiment will be described in concrete referring to FIG. 37. FIG. 37 shows an example of the intermittence time determination table. This table is comprised by a matrix of the respective zone axis and the momentum axis. And in each zone, a plurality of P cycles are set.

The intermittence time determination part 4 determines the intermittence time referring to this intermittence time determination table. In concrete, the P cycle to which the adhesion to be the target to determine the intermittence time corresponds and the momentum of the detected adhesion are obtained, and the intermittence time is determined referring to the intermittence time determination table shown in FIG. 37. In order to execute such control, it is preferable that the adhesion cycle detection part 2 stores the applicable P cycle and the waveform momentum in the memory as a history for each adhesion. The intermittence time determination part 4 can obtain the P cycle and the waveform momentum by referring to such a history of adhesion.

As an example of the control, the intermittence tome of each adhesion may be acquired from the P cycle and the waveform momentum for a plurality number of times of (3 times, for example) of adhesion and the actual intermittence time may be determined by averaging the three times of intermittence time thus acquired. By constituting in this way, hunting in fluctuation of the intermittence time can be prevented. At the same time, change of the rainfall state can be responded more closely.

Also, when an edge is generated, the edge registration part 6 may register the P cycle and the waveform momentum at the edge generation in the edge registration table. The intermittence time determination part 4 may obtain the P cycle and the waveform momentum at the edge generation by referring to the edge registration table.

By constituting in this way, in the fourth preferred embodiment of the present invention, by providing a plurality of P cycles in each zone and by determining the adhesion cycle for each P cycle, the intermittence time can be determined in close response to fluctuation of the adhesion cycle.

INDUSTRIAL APPLICABILITY

As described above, according to the present invention, unnecessary switch-over of the wiping state of the wiper can be restricted, and change of the rainfall situation can be smoothly responded. Also, the wiping operation of the wiper more matching the sense of a driver can be realized.

The invention claimed is:

1. A method for controlling operation of a wiper by reflecting light emitted from a light emitting element on a detection surface provided at a part of a wiper wiping area of a windshield glass of a vehicle and by detecting a state of said detection surface by receiving said reflected light by a light receiving element, comprising the steps of:
(a) detecting an adhesion cycle of a raindrop adhering on said detection surface;
(b) determining a current adhesion cycle to be the basis when determining intermittence time of said wiper based on said detected raindrop adhesion cycle;
(c) determining said wiper intermittence time based on said current adhesion cycle;
(d) detecting said raindrop adhesion cycle shorter than said current adhesion cycle;
(e) changing the current adhesion cycle to a shorter adhesion cycle if said raindrop adhesion cycle shorter than said current adhesion cycle is detected a predetermined number of times; and
(f) determining said wiper intermittence time based on the changed current adhesion cycle.

2. A method for controlling a wiper according to claim 1, further comprising the steps of:
(g) detecting said raindrop adhesion cycle longer than said current adhesion cycle;
(h) changing the current adhesion cycle to a longer adhesion cycle if said raindrop adhesion cycle longer than said current adhesion cycle is detected a predetermined number of times; and
(i) determining said wiper intermittence time based on the changed current adhesion cycle.

3. A method for controlling a wiper according to claim 1 or 2, further comprising the steps of:
if said raindrop adhesion cycle shorter than said current adhesion cycle was detected in said step (d), determining a temporary intermittence time based on said raindrop adhesion cycle shorter than said current adhesion cycle and maintaining said temporary intermittence time for a predetermined period of time as said wiper intermittence time; and
returning said wiper intermittence time to an intermittence time determined based on said current adhesion cycle after said predetermined period of time has finished.

4. A method for controlling a wiper according to any one of claim 1 or 2 further comprising the steps of:
(j) determining the size of a raindrop adhering on said detection surface by evaluating fluctuation of a waveform of an output signal of said light receiving element;
(k) determining if said raindrop size is a predetermined threshold value or more and raindrop adhesion onto said detection surface has continued a predetermined number of times or not; and
(l) switching the wiping state of said wiper to continuous wiping if the determination in said step (k) is yes.

5. A method for controlling a wiper according to any one of claim 1 or 2, further comprising the steps of:
(m) determining the size of a raindrop adhering on said detection surface by evaluating fluctuation of a waveform of an output signal of said light receiving element; and
(n) determining said wiper intermittence time by combining said determined raindrop size and said current adhesion cycle or determining said temporary intermittence time by combining said determined raindrop size and said raindrop adhesion cycle shorter than said current adhesion cycle.

6. A wiper control device for controlling operation of said wiper by reflecting light emitted from a light emitting element on a detection surface provided at a part of a wiper wiping area of a windshield glass of a vehicle and by detecting a state of said detection surface by receiving said reflected light by a light receiving element, comprising:
an adhesion cycle detection part for detecting an adhesion cycle of a raindrop adhering on said detection surface;

a zone transition control part for determining a current adhesion cycle to be the basis when determining said wiper intermittence time based on said detected raindrop adhesion cycle; and an intermittence time determination part for determining said wiper intermittence time based on said current adhesion cycle, wherein said adhesion cycle detection part detects said raindrop adhesion cycle shorter than said current adhesion cycle, said zone transition control part changes said current adhesion cycle to a shorter adhesion cycle when said raindrop adhesion cycle shorter than said current adhesion cycle is detected a predetermined number of times, and said intermittence time determination part determines said wiper intermittence time based on the changed current adhesion cycle.

7. A wiper control device according to claim 6, wherein said adhesion cycle detection part detects said raindrop adhesion cycle longer than said current adhesion cycle, said zone transition control part changes said current adhesion cycle to a longer adhesion cycle when said raindrop adhesion cycle longer than said current adhesion cycle is detected a predetermined number of times, and said intermittence time determination part determines said wiper intermittence time based on the changed current adhesion cycle.

8. A wiper control device according to claim 6 or 7, wherein said intermittence time determination part determines a temporary intermittence time based on said raindrop adhesion cycle shorter than said current adhesion cycle, maintains said temporary intermittence time for a predetermined period of time as said wiper intermittence time, and returns said wiper intermittence time to an intermittence time determined based on said current adhesion cycle after said predetermined period of time has finished, if said adhesion cycle detection part detected said raindrop adhesion cycle shorter than said current adhesion cycle.

9. A wiper control device according to any one of claim 6 or 7, further comprising:

a fluctuation evaluation part for evaluating fluctuation of a waveform of an output signal of said light receiving element to determine the size of a raindrop adhering on said detection surface; and a continuous wiping determination part for determining if said raindrop size is at a predetermined threshold value or more and the raindrop adhesion to said detection surface has continued a predetermined number of times and if the determination is yes, for switching the wiping state of said wiper to continuous wiping.

10. A wiper control device according to any one of claim 6 or 7, further comprising a fluctuation evaluation part for evaluating fluctuation of a waveform of an output signal of said light receiving element to determine the size of a raindrop adhering on said detection surface;

wherein said intermittence time determination part determines said wiper intermittence time by combining said determined raindrop size and said current adhesion cycle or determines said temporary intermittence time by combining said determined raindrop size and said raindrop adhesion cycle shorter than said current adhesion cycle.

* * * * *